(12) United States Patent
Sutterlin, III et al.

(10) Patent No.: US 12,220,325 B2
(45) Date of Patent: Feb. 11, 2025

(54) SPINAL FIXATION DEVICE

(71) Applicants: K2M, Inc., Leesburg, VA (US); Ohio State Innovation Foundation, Columbus, OH (US)

(72) Inventors: Chester Evan Sutterlin, III, Sarasota, FL (US); Ehud Mendel, Columbus, OH (US); Michael Finn, Aurora, CO (US); Clint Boyd, Leesburg, VA (US); Scott Jones, Mcmurray, PA (US); Todd Wallenstein, Ashburn, VA (US); Jacob M. Buchowski, St. Louis, MO (US)

(73) Assignees: K2M, Inc., Leesburg, VA (US); Ohio State Innovation Foundation, Columbus, OH (US)

( * ) Notice: Subject to any disclaimer, the term of this patent is extended or adjusted under 35 U.S.C. 154(b) by 150 days.

(21) Appl. No.: 17/505,371

(22) Filed: Oct. 19, 2021

(65) Prior Publication Data

US 2022/0039967 A1 Feb. 10, 2022

Related U.S. Application Data

(60) Continuation of application No. 16/379,331, filed on Apr. 9, 2019, now Pat. No. 11,173,041, which is a (Continued)

(51) Int. Cl.
*A61F 2/44* (2006.01)
*A61F 2/46* (2006.01)
*A61F 2/30* (2006.01)

(52) U.S. Cl.
CPC .............. *A61F 2/4465* (2013.01); *A61F 2/44* (2013.01); *A61F 2/4611* (2013.01);
(Continued)

(58) Field of Classification Search
None
See application file for complete search history.

(56) References Cited

U.S. PATENT DOCUMENTS 3,374,011 A 3/1968 Schipper
3,402,947 A 9/1968 Lewis
(Continued)

FOREIGN PATENT DOCUMENTS

DE 19804765 A1 8/1999
EP 1878408 A1 1/2008
(Continued)

OTHER PUBLICATIONS

European Search Report for EP15194277 dated Feb. 23, 2016.
(Continued)

*Primary Examiner* — Sameh R Boles
(74) *Attorney, Agent, or Firm* — Lerner David LLP

(57) ABSTRACT

A spinal fixation device includes an outer housing and an end plate assembly coupled with the outer housing. The outer housing defines an aperture and a longitudinal axis. At least a portion of the end plate assembly is slidably received within the outer housing. The end plate assembly includes a first end plate configured to engage a vertebral body, wherein the end plate assembly is selectively movable between a first position in which the first end plate is spaced apart from the outer housing and a second position in which the first end plate is adjacent the outer housing. Further, the first end plate is selectively adjustable to an angular orientation of a plurality of angular orientations with respect to the longitudinal axis of the outer housing.

19 Claims, 21 Drawing Sheets

Related U.S. Application Data division of application No. 14/936,911, filed on Nov. 10, 2015, now Pat. No. 10,292,832, which is a continuation-in-part of application No. 14/212,236, filed on Mar. 14, 2014, now Pat. No. 9,707,096.

(60) Provisional application No. 62/078,666, filed on Nov. 12, 2014, provisional application No. 61/781,837, filed on Mar. 14, 2013.

(52) U.S. Cl.
CPC .............. *A61F 2002/30373* (2013.01); *A61F 2002/30392* (2013.01); *A61F 2002/30405* (2013.01); *A61F 2002/30495* (2013.01); *A61F 2002/30523* (2013.01); *A61F 2002/30538* (2013.01); *A61F 2002/30556* (2013.01); *A61F 2002/30579* (2013.01); *A61F 2002/30601* (2013.01); *A61F 2002/3068* (2013.01); *A61F 2002/30904* (2013.01); *A61F 2002/3093* (2013.01); *A61F 2/4603* (2013.01); *A61F 2002/4627* (2013.01); *A61F 2002/4638* (2013.01); *A61F 2310/00017* (2013.01); *A61F 2310/00023* (2013.01); *A61F 2310/00029* (2013.01); *A61F 2310/00179* (2013.01)

(56) References Cited

U.S. PATENT DOCUMENTS

| | | |
|---|---|---|
| 3,588,023 A | 6/1971 | Cohen |
| 3,893,730 A | 7/1975 | Homier et al. |
| 4,387,926 A | 6/1983 | Van Eerden et al. |
| 4,554,914 A | 11/1985 | Kapp et al. |
| 4,938,319 A | 7/1990 | Ernst |
| 5,053,036 A | 10/1991 | Perren et al. |
| 5,108,066 A | 4/1992 | Lundstrom |
| 5,236,460 A | 8/1993 | Barber |
| 5,290,312 A | 3/1994 | Kojimoto et al. |
| 5,336,223 A | 8/1994 | Rogers |
| 5,360,430 A | 11/1994 | Lin |
| 5,458,641 A | 10/1995 | Ramirez Jimenez |
| 5,520,690 A | 5/1996 | Errico et al. |
| 5,547,308 A | 8/1996 | Wright |
| 5,571,190 A | 11/1996 | Ulrich et al. |
| 5,571,192 A | 11/1996 | Schonhoffer |
| 5,702,455 A | 12/1997 | Saggar |
| 5,723,013 A | 3/1998 | Jeanson et al. |
| 5,738,685 A | 4/1998 | Halm et al. |
| 5,776,198 A | 7/1998 | Rabbe et al. |
| 5,885,286 A | 3/1999 | Sherman et al. |
| 5,888,014 A | 3/1999 | Lung et al. |
| 5,901,798 A | 5/1999 | Herrera et al. |
| 5,904,683 A | 5/1999 | Pohndorf et al. |
| 5,980,522 A | 11/1999 | Koros et al. |
| 5,989,290 A | 11/1999 | Biedermann et al. |
| 6,074,391 A | 6/2000 | Metz-Stavenhagen et al. |
| 6,099,531 A | 8/2000 | Bonutti |
| 6,110,172 A | 8/2000 | Jackson |
| 6,132,434 A | 10/2000 | Sherman et al. |
| 6,176,881 B1 | 1/2001 | Schar et al. |
| 6,179,514 B1 | 1/2001 | Cheng |
| 6,183,517 B1 | 2/2001 | Suddaby |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,235,062 B1 | 5/2001 | Gramnas |
| 6,241,769 B1 | 6/2001 | Nicholson et al. |
| 6,254,602 B1 | 7/2001 | Justis |
| 6,273,888 B1 | 8/2001 | Justis |
| 6,296,642 B1 | 10/2001 | Morrison et al. |
| 6,296,665 B1 | 10/2001 | Strnad et al. |
| 6,302,888 B1 | 10/2001 | Mellinger et al. |
| 6,332,895 B1 | 12/2001 | Suddaby |
| 6,342,074 B1 | 1/2002 | Simpson |
| 6,364,880 B1 | 4/2002 | Michelson |
| 6,375,683 B1 | 4/2002 | Crozet et al. |
| 6,395,034 B1 | 5/2002 | Suddaby |
| 6,419,705 B1 | 7/2002 | Erickson |
| 6,423,063 B1 | 7/2002 | Bonutti |
| 6,440,170 B1 | 8/2002 | Jackson |
| 6,500,178 B2 | 12/2002 | Zucherman et al. |
| 6,524,341 B2 | 2/2003 | Lang et al. |
| 6,558,423 B1 | 5/2003 | Michelson |
| 6,562,074 B2 | 5/2003 | Gerbec et al. |
| 6,610,090 B1 | 8/2003 | Bohm et al. |
| 6,616,695 B1 | 9/2003 | Crozet et al. |
| 6,629,998 B1 | 10/2003 | Lin |
| 6,648,917 B2 | 11/2003 | Gerbec et al. |
| 6,660,038 B2 | 12/2003 | Boyer et al. |
| 6,663,060 B1 | 12/2003 | Gifford, Sr. |
| 6,716,214 B1 | 4/2004 | Jackson |
| 6,730,088 B2 | 5/2004 | Yeh |
| 6,752,832 B2 | 6/2004 | Neumann |
| 6,770,096 B2 | 8/2004 | Bolger et al. |
| 6,827,719 B2 | 12/2004 | Ralph et al. |
| 6,830,589 B2 | 12/2004 | Erickson |
| 6,834,840 B1 | 12/2004 | Metz et al. |
| 6,835,196 B2 | 12/2004 | Biedermann et al. |
| 6,837,889 B2 | 1/2005 | Shluzas |
| 6,843,791 B2 | 1/2005 | Serhan |
| 6,852,129 B2 | 2/2005 | Gerbec et al. |
| 6,863,673 B2 | 3/2005 | Gerbec et al. |
| 6,866,682 B1 | 3/2005 | An et al. |
| 6,869,112 B2 | 3/2005 | Guidetti |
| 6,869,433 B2 | 3/2005 | Glascott |
| 6,884,244 B1 | 4/2005 | Jackson |
| 6,893,443 B2 | 5/2005 | Frigg et al. |
| 6,896,677 B1 | 5/2005 | Lin et al. |
| 6,908,485 B2 | 6/2005 | Crozet et al. |
| 6,918,911 B2 | 7/2005 | Biedermann et al. |
| 6,945,975 B2 | 9/2005 | Dalton |
| 6,972,019 B2 | 12/2005 | Michelson |
| 6,984,234 B2 | 1/2006 | Bray |
| 7,001,385 B2 | 2/2006 | Bonutti |
| 7,025,787 B2 | 4/2006 | Bryan et al. |
| 7,033,394 B2 | 4/2006 | Michelson |
| 7,041,135 B2 | 5/2006 | Michelson |
| 7,052,499 B2 | 5/2006 | Steger et al. |
| 7,056,343 B2 | 6/2006 | Schafer et al. |
| 7,077,864 B2 | 7/2006 | Byrd, III et al. |
| 7,086,631 B2 | 8/2006 | Lee et al. |
| 7,087,057 B2 | 8/2006 | Konieczynski et al. |
| 7,094,257 B2 | 8/2006 | Mujwid et al. |
| 7,156,874 B2 | 1/2007 | Paponneau et al. |
| 7,175,624 B2 | 2/2007 | Konieczynski et al. |
| 7,229,443 B2 | 6/2007 | Eberlein et al. |
| 7,285,134 B2 | 10/2007 | Berry et al. |
| 7,318,825 B2 | 1/2008 | Butler et al. |
| 7,445,627 B2 | 11/2008 | Hawkes et al. |
| 7,527,640 B2 | 5/2009 | Ziolo et al. |
| 7,531,002 B2 | 5/2009 | Sutton et al. |
| 7,544,208 B1 | 6/2009 | Mueller et al. |
| 7,611,104 B1 | 11/2009 | Gifford, Sr. |
| 7,618,456 B2 | 11/2009 | Mathieu et al. |
| 7,651,517 B2 | 1/2010 | Konieczynski et al. |
| 7,691,147 B2 | 4/2010 | Gutlin et al. |
| 7,862,616 B2 | 1/2011 | Lechmann et al. |
| 8,137,405 B2 | 3/2012 | Kostuik et al. |
| 8,353,961 B2 | 1/2013 | McClintock et al. |
| 8,377,101 B2 | 2/2013 | Barrus et al. |
| 8,439,977 B2 | 5/2013 | Kostuik et al. |
| 8,585,761 B2 | 11/2013 | Theofilos |
| 8,663,330 B2 | 3/2014 | McClintock et al. |
| 8,673,011 B2 | 3/2014 | Theofilos et al. |
| 8,801,791 B2 | 8/2014 | Soo et al. |
| 8,814,919 B2 | 8/2014 | Barrus et al. |
| 8,920,471 B2 | 12/2014 | Barrus et al. |
| 2001/0021851 A1 | 9/2001 | Eberlein et al. |
| 2002/0032443 A1 | 3/2002 | Sherman et al. |
| 2002/0128654 A1 | 9/2002 | Steger et al. |
| 2002/0161441 A1 | 10/2002 | Lang et al. |
| 2003/0130737 A1 | 7/2003 | McGahan et al. |
| 2003/0130739 A1 | 7/2003 | Gerbec et al. |

(56) References Cited

U.S. PATENT DOCUMENTS

| | | |
|---|---|---|
| 2003/0181980 A1 | 9/2003 | Berry et al. |
| 2004/0186569 A1 | 9/2004 | Berry |
| 2004/0247379 A1 | 12/2004 | Guidetti |
| 2005/0060034 A1 | 3/2005 | Berry et al. |
| 2005/0085910 A1 | 4/2005 | Sweeney |
| 2005/0209697 A1 | 9/2005 | Paponneau et al. |
| 2005/0218275 A1 | 10/2005 | Keating |
| 2005/0273173 A1 | 12/2005 | Gordon et al. |
| 2006/0041260 A1 | 2/2006 | Orbay |
| 2006/0074490 A1 | 4/2006 | Sweeney |
| 2006/0100710 A1 | 5/2006 | Gutlin et al. |
| 2006/0122701 A1 | 6/2006 | Kiester |
| 2006/0129244 A1 | 6/2006 | Ensign |
| 2006/0149251 A1 | 7/2006 | Ziolo et al. |
| 2006/0149385 A1 | 7/2006 | McKay |
| 2006/0173456 A1 | 8/2006 | Hawkes et al. |
| 2006/0200244 A1 | 9/2006 | Assaker |
| 2006/0212118 A1 | 9/2006 | Abernathie |
| 2006/0217715 A1 | 9/2006 | Serhan et al. |
| 2006/0241762 A1 | 10/2006 | Kraus |
| 2006/0241770 A1 | 10/2006 | Rhoda et al. |
| 2006/0271047 A1 | 11/2006 | Jackson |
| 2006/0276792 A1 | 12/2006 | Ensign et al. |
| 2007/0010887 A1 | 1/2007 | Williams et al. |
| 2007/0032871 A1 | 2/2007 | Michelson |
| 2007/0073298 A1 | 3/2007 | Beutter et al. |
| 2007/0093817 A1 | 4/2007 | Barrus et al. |
| 2007/0100340 A1 | 5/2007 | Lange et al. |
| 2007/0106231 A1 | 5/2007 | Snow et al. |
| 2007/0162126 A1 | 7/2007 | Karahalios et al. |
| 2007/0191954 A1* | 8/2007 | Hansell ............... A61F 2/44 623/17.15 |
| 2007/0219635 A1 | 9/2007 | Mathieu et al. |
| 2007/0250171 A1 | 10/2007 | Bonin |
| 2007/0255408 A1 | 11/2007 | Castleman et al. |
| 2007/0270964 A1 | 11/2007 | Strohkirch et al. |
| 2007/0270968 A1 | 11/2007 | Baynham et al. |
| 2007/0282441 A1 | 12/2007 | Stream et al. |
| 2008/0009946 A1 | 1/2008 | Douget et al. |
| 2008/0021555 A1 | 1/2008 | White et al. |
| 2008/0114467 A1 | 5/2008 | Capote et al. |
| 2008/0125864 A1 | 5/2008 | de Villiers et al. |
| 2008/0147193 A1 | 6/2008 | Matthis et al. |
| 2008/0167720 A1 | 7/2008 | Melkent |
| 2008/0249624 A1 | 10/2008 | Josimovic-Alasevic et al. |
| 2008/0249625 A1 | 10/2008 | Waugh et al. |
| 2008/0288071 A1 | 11/2008 | Biyani et al. |
| 2010/0005715 A1 | 1/2010 | Allsop et al. |
| 2010/0137919 A1 | 6/2010 | Wolter |
| 2010/0318092 A1 | 12/2010 | Butler et al. |
| 2010/0324686 A1* | 12/2010 | Gerner ............... A61F 2/44 623/17.16 |
| 2011/0160861 A1 | 6/2011 | Jimenez et al. |
| 2011/0208248 A1 | 8/2011 | Barrus et al. |
| 2012/0179255 A1* | 7/2012 | DeFalco ............ A61F 2/4611 623/17.11 |
| 2014/0135931 A1 | 5/2014 | Popa et al. |
| 2014/0277503 A1 | 9/2014 | Mendel et al. |

FOREIGN PATENT DOCUMENTS

| | | |
|---|---|---|
| FR | 2902315 A1 | 12/2007 |
| SU | 01560184 A1 | 4/1990 |
| WO | 98/46173 | 10/1998 |
| WO | 03032812 A2 | 4/2003 |
| WO | 2008005627 A2 | 1/2008 |
| WO | 2009023016 A1 | 2/2009 |

OTHER PUBLICATIONS

European Comminucation issued in corresponding European Appln No. 15194277.8 dated Feb. 23, 2017.
European Search Report dated May 28, 2009 from corresponding EP Appln. No. EP09152270.6 filed Feb. 6, 2009.
International Search Report from PCT/US2009/038787 dated May 27, 2009.
International Search Report for PCT/US2009/038780 dated Nov. 13, 2009.
Extended European Search Report including Written Opinion for EP09724564 dated Dec. 7, 2012.
Extended European Search Report including Written Opinion for EP15194277.8 dated Mar. 3, 2016.
Australian Examination Report for Application No. 2015255166 dated Sep. 17, 2019, 1 page.
Australian Examination Report for Application No. 2015255166, dated Aug. 11, 2020, 1 page.

* cited by examiner

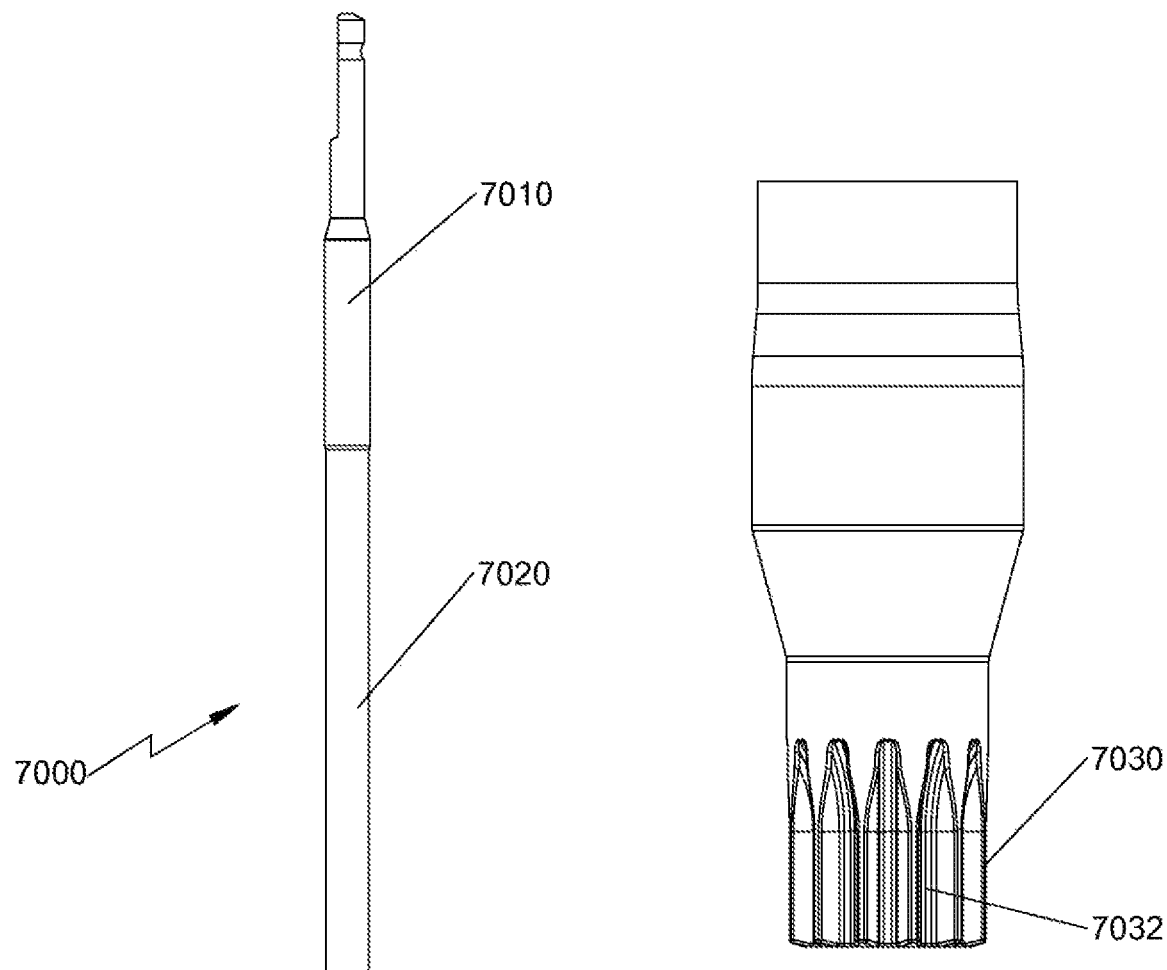
FIG. 13 C
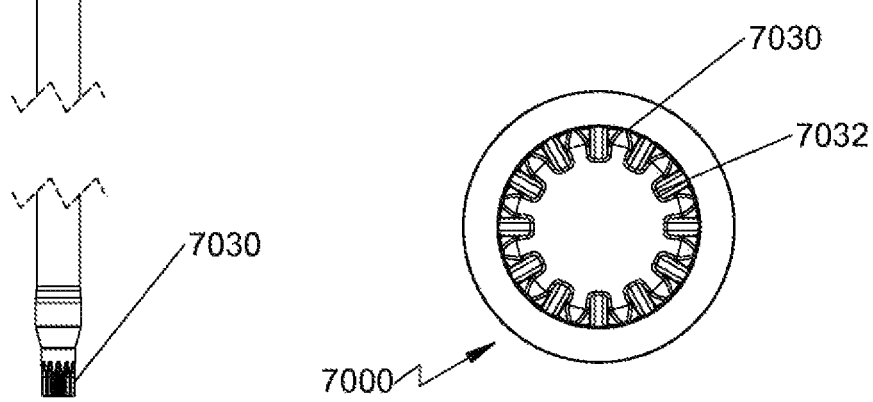
FIG. 13 B
FIG. 13 A

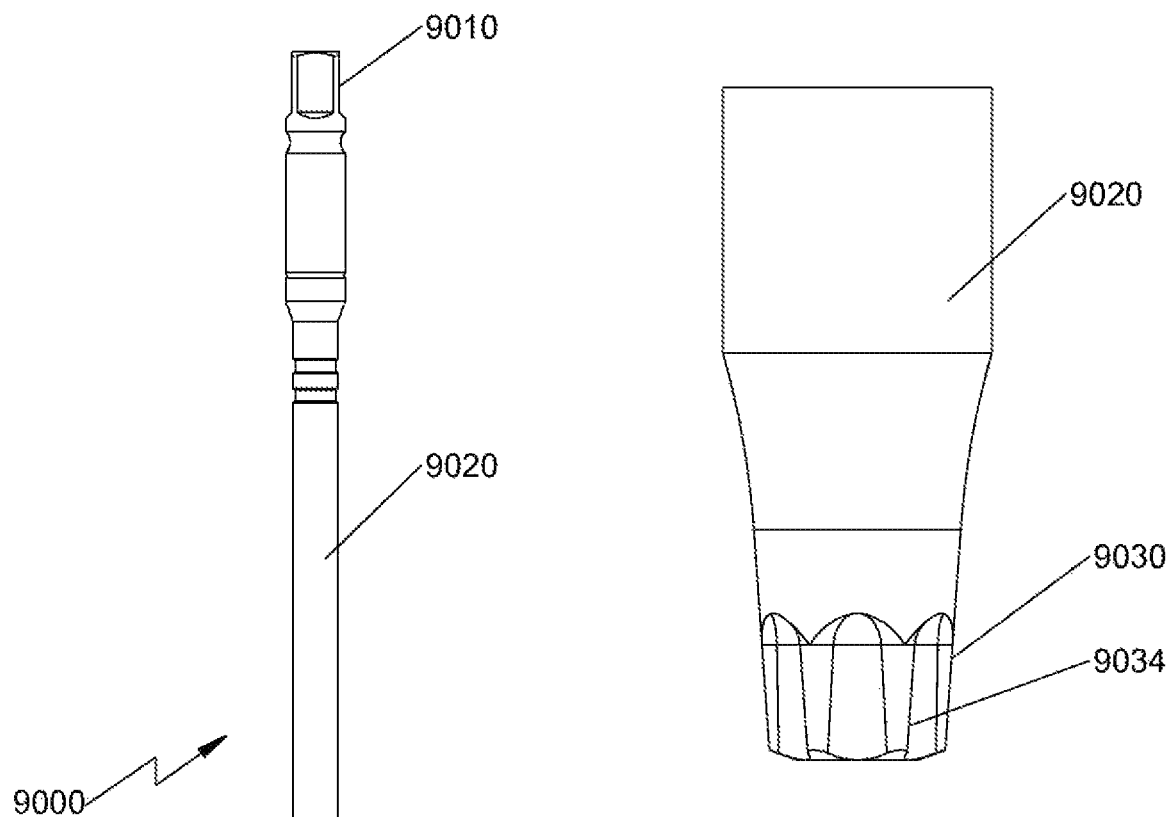
FIG. 15 C
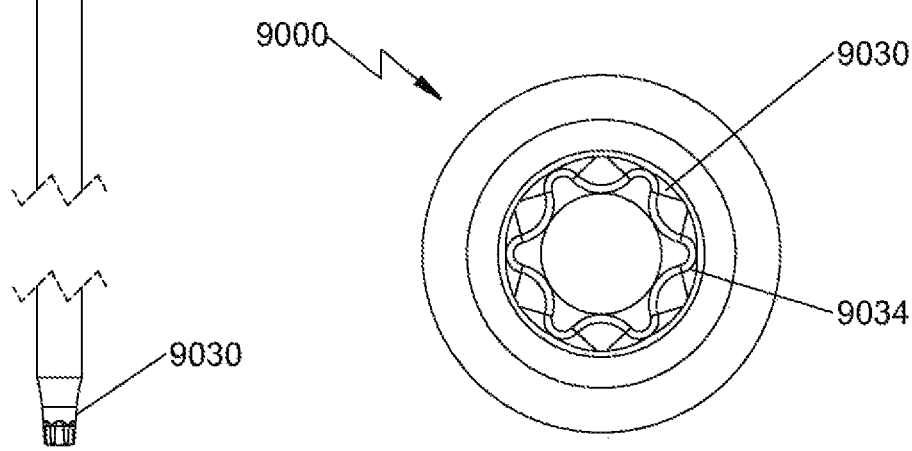
FIG. 15 B
FIG. 15 A

SPINAL FIXATION DEVICE

CROSS-REFERENCE TO RELATED APPLICATION

This application is a continuation of U.S. patent application Ser. No. 16/379,331, filed on Apr. 9, 2019, which is a divisional of U.S. application Ser. No. 14/936,911, filed Nov. 10, 2015, now U.S. Pat. No. 10,292,832, which is a continuation-in-part of U.S. patent application Ser. No. 14/212,236, filed on Mar. 14, 2014, now U.S. Pat. No. 9,707,096, which claims the benefit of U.S. Provisional Application No. 62/078,666, filed on Nov. 12, 2014, and U.S. Provisional Application No. 61/781,837, filed on Mar. 14, 2013. The disclosures of each of these prior applications are incorporated by reference herein.

BACKGROUND

Technical Field

The present disclosure relates to an apparatus for treating spinal conditions, and more particularly, to an intervertebral implant.

Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs. Inter-vertebral discs provide flexibility to the spine and act as shock absorbers during activity. A small opening (foramen) located in each vertebra allows passage of the spinal cord. When the vertebrae are properly aligned, the spinal cord passes through without a problem. However, when the vertebrae are misaligned or a constriction is formed in the spinal canal, nerves of the spinal cord may get compressed and may cause back pain, leg pain, or other neurological disorders.

Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of adjacent vertebral bodies. Scientists and clinicians have developed a number of devices and methods for decompressing spinal nerves. Improvements to these methods and devices are nevertheless still possible. Reference may be made to U.S. Patent Publication No. 2014/0277503 filed on Mar. 14, 2014, entitled "Spinal Fixation Device," the entire content of which is incorporated herein by reference, for a detailed discussion of the construction and operation of a spinal fixation system and an instrumentation for use therewith.

Furthermore, intervertebral spacer implants used as a stand-alone device or provided in an assembly including a retention mechanism to help alleviate expulsion and movement of the implant when placed in the spine, are well known. Such implant assemblies are advantageous in providing an implant that is easier to insert in the spine. Intervertebral spacer implant assemblies which include a spacer and a plate, where the plate comprises a supplemental or alternative retention mechanism having one or more holes in the anterior end of the plate that are directed toward the superior, inferior or both end plates of adjacent vertebrae are also known in the art. Such implants are used to stabilize and immobilize the spinal segments in the treatment of single or multi-level degenerative disc disease, spinal stenosis, and failed previous fusions, as well as other spine conditions.

To meet the problem of preventing expulsion of the interbody device and for providing stability to the anatomy, a need exists for an spinal fixation device that can be secured to the spine and provide anterior column support and stabilization, while providing a maximum fusion area.

SUMMARY

In accordance with an embodiment of the present disclosure, there is provided a spinal fixation device including an outer housing and an end plate assembly coupled with the outer housing. The outer housing defines an aperture and a longitudinal axis. At least a portion of the end plate assembly is slidably received within the outer housing through the aperture. The end plate assembly includes a first end plate configured to engage a vertebral body, wherein the end plate assembly is selectively movable between a first position in which the first end plate is spaced apart from the outer housing and a second position in which the first end plate is adjacent the outer housing. Further, the first end plate is selectively adjustable to an angular orientation of a plurality of angular orientations with respect to the longitudinal axis of the outer housing.

In an embodiment, the end plate assembly may include first and second elongate members operatively coupled to the first end plate such that axial movement of the first and second elongate members in tandem causes axial displacement of the first end plate, and relative movement between the first and second elongate members transitions the first end plate from a first angular orientation to a second angular orientation.

In another embodiment, the spinal fixation device may include a mounting assembly operatively supporting the first and second elongate members in the outer housing. The mounting assembly may be releasably secured with the outer housing. In yet another embodiment, the mounting assembly may include a retaining housing and first and second rotatable members rotatably supported in the retaining housing. The first and second rotatable members may be operatively coupled with the first and second elongate members of the end plate assembly. The first and second rotatable members of the mounting assembly may be spaced apart from each other to define a gap therebetween.

In an embodiment, each of the first and second rotatable members of the mounting assembly may include circumferentially arranged teeth opposing each other. The first rotatable member of the mounting assembly may include inner threads in a first orientation and the second rotatable member of the mounting assembly may include inner threads in a second orientation opposite to the first orientation.

The outer housing may define a plurality of bores. In particular, at least one bore of the plurality of bores may be in communication with the gap defined between the first and second rotatable members of the mounting assembly. The plurality of bores may be circumferentially arranged about the outer housing. The plurality of bores may be arranged along a length of the outer housing.

In accordance with another embodiment of present disclosure, there is provided a surgical kit including a spinal fixation device and a surgical instrument. The spinal fixation device includes an outer housing and an end plate assembly. The end plate assembly is coupled with the outer housing. At least a portion of the end plate assembly is slidably received within the outer housing through an aperture of the outer housing. The end plate assembly includes a first end plate configured to engage a vertebral body, wherein the end plate assembly is selectively movable between a first position in which the first end plate is spaced apart from the outer housing and a second position in which the first end plate is adjacent the outer housing. In addition, the first end plate is selectively adjustable to an angular orientation of a plurality of angular orientations with respect to the outer housing. The surgical instrument defines a channel extending therethrough. The surgical instrument defines an engaging portion configured to securely engage the outer housing of the spinal fixation device.

In an embodiment, the surgical instrument may include a height adjusting driver rotatably extending through the channel of the surgical instrument. The height adjusting driver may include an engaging portion having teeth configured to engage the circumferentially arranged teeth of the first and second rotatable members of the mounting assembly, whereby rotation of the height adjusting driver causes rotation of the first and second rotatable members of the mounting assembly.

In another embodiment, the surgical instrument may further include an angle adjusting driver rotatably extending through the channel of the surgical instrument. The angle adjusting driver may include an engaging portion having teeth configured to engage the circumferentially arranged teeth of one of the first or second rotatable members of the mounting assembly, whereby rotation of the angle adjusting driver causes rotation of the one of the first or second rotatable members of the mounting assembly.

In yet another embodiment, the kit may further include a rod connector having an anchoring portion coupled with the outer housing of the spinal fixation device and a head portion having a recessed portion configured to receive a spinal rod. In particular, the rod connector may define a channel therethrough. In addition, the head portion of the rod connector may define a bore in communication with the channel.

In yet another embodiment, the kit may further include a drug delivery assembly including a drug reservoir securely coupled with the outer housing of the spinal fixation device, a supply port, and a catheter in fluid communication with the supply port and the drug reservoir.

In yet another embodiment, the kit may further include a shield attachable to the spinal fixation device. In particular, the shield may be configured to reduce radiation to a spinal cord. Alternatively, the shield may include slow releasing medicament.

BRIEF DESCRIPTION OF THE DRAWINGS

The above and other aspects and features of the present disclosure will become more apparent in light of the following detailed description when taken in conjunction with the accompanying drawings in which:

FIG. 13A is a side view of a height adjusting driver for use with the insertion instrument of FIG. 10;

FIG. 13B is a top view of the height adjusting driver of FIG. 13A;

FIG. 13C is a partial side view of a distal portion of the height adjusting driver of FIG. 13A;

FIG. 15A is a side view of a tapered driver for use with the insertion instrument of FIG. 10;

FIG. 15B is a top view of the tapered driver of FIG. 15A;

FIG. 15C is a partial side view of a distal portion of the tapered driver of FIG. 15A;

FIG. 21a is a perspective view of the spinal fixation device of FIG. 1 and the rod connector of FIG. 20a;

FIG. 21b is a perspective view of the spinal fixation device and the rod connector of FIG. 21a illustrating polyaxial rotation of the rod connector;

DETAILED DESCRIPTION OF THE EMBODIMENTS

Figure 1:
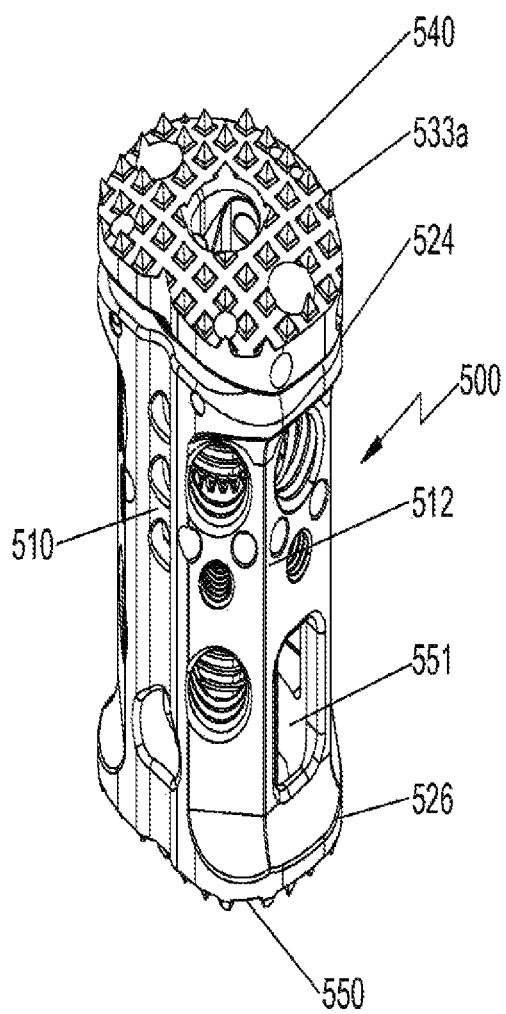
FIG. 1 is a perspective view of a spinal fixation device in accordance with an embodiment of the present disclosure.
Figure 2:
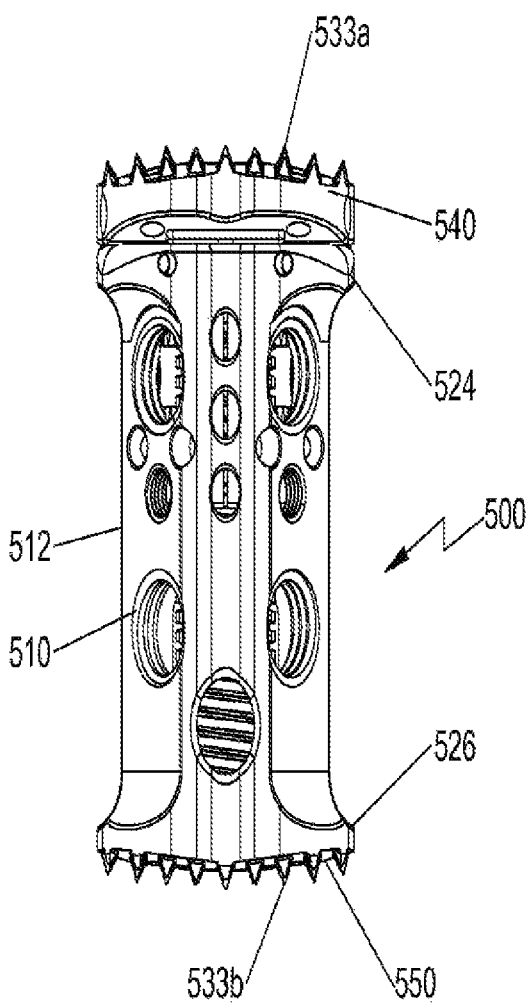
FIG. 2 is a rear view of the spinal fixation device of FIG. 1.
Figure 3:
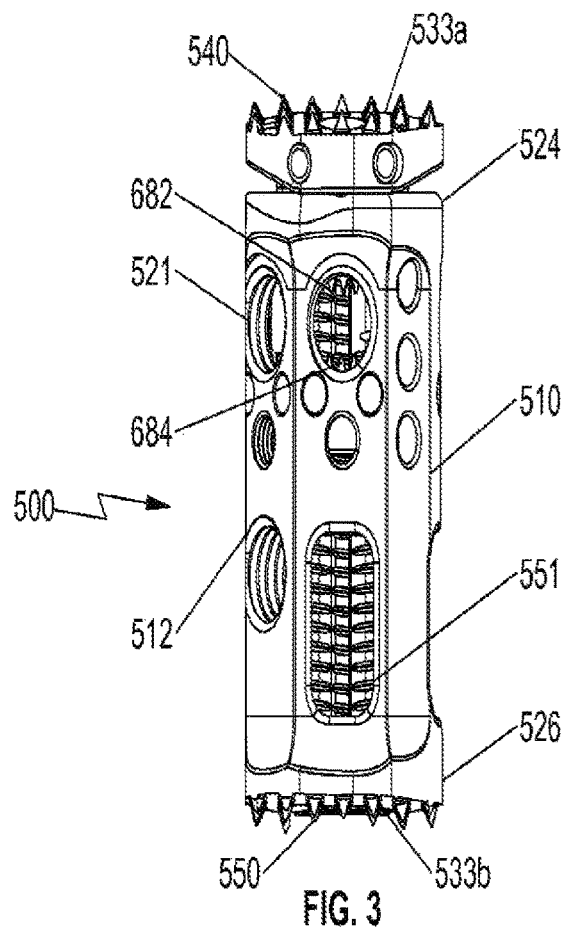
FIG. 3 is a side view of the spinal fixation device of FIG. 1.
Figure 4:
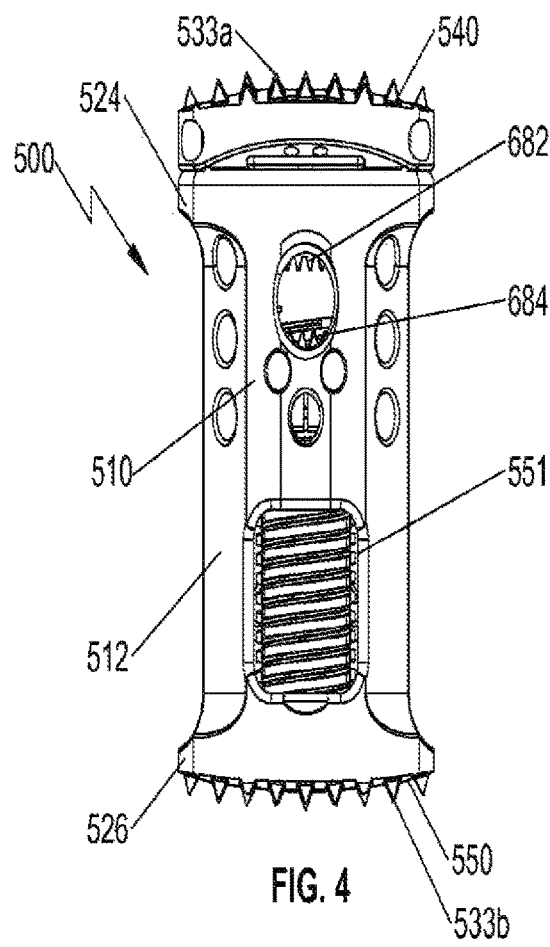
FIG. 4 is a front view of the spinal fixation device of FIG. 1.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" or "cranial" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

With reference to FIGS. 1-4 and 6, an embodiment of the present disclosure is shown generally as a spinal fixation device 500 configured and adapted to be positioned between vertebral bodies to support vertebral bodies and to promote spinal fusion. By way of example, spinal fixation device 500 may be inserted into the patient laterally, posteriorly, anteriorly, or obliquely. Additionally, spinal fixation device 500 may be inserted into the patient through procedures such as, e.g., posterior lumbar interbody fusion (PLIF), transforaminal lumbar interbody fusion (TLIF), lateral lumbar interbody fusion (LLIF), oblique lumbar interbody fusion (OLIF), or lateral extracavitary (LECA) procedures. Spinal fixation device 500 includes an outer housing 510 and an end plate assembly 560 interchangeably coupled with outer housing 510. Outer housing 510 includes a second end plate 550. End plate assembly 560 includes a first end plate 540, first and second elongate members 666, 668 operatively supporting first end plate 540, and a mounting assembly 600 operatively supporting first and second elongate members 666, 668. First and second end plates 540, 550 are configured to engage end plates of adjacent vertebral bodies. In particular, first and second end plates 540, 550 are configured to engage, e.g., endplates of superior and inferior vertebral bodies, respectively. Each of first and second end plates 540, 550 may include a plurality of pyramidal shaped spikes 533a, 533b (i.e., tetrahedrons) to aid in securing spinal fixation device 500 to the adjacent vertebral bodies for enhanced gripping of the vertebral bodies and minimizing movement of spinal fixation device 500 relative to the vertebral bodies. However, it is also contemplated that each of first and second end plates 540, 550 may include ridges or similar projections to aid in securing spinal fixation device 500 to the vertebral bodies.

End plate assembly 560 is configured as a modular assembly that is interchangeably mounted in outer housing 510. For example, a plurality of end plate assemblies 560 may be provided with varying parameters such as, e.g., footprint and lordosis, such that the clinician may selectively attach a desired end plate assembly 560 to outer housing 510 to meet the needs of each patient or surgical procedure being performed. In this manner, end plate assembly 560 may be tailored to achieve a desired lordosis of a first end plate 540 and a desired axial spacing between outer housing 510 and first end plate 540, as will be discussed hereinbelow.

Spinal fixation device 500 may be made of titanium, titanium alloy, stainless steel, allograft bone, autologous bone graft, polyetheretherketone (PEEK), cobalt chrome, polymeric materials, a combination thereof, or any other suitable biocompatible material. In particular, spinal fixation device 500 may be formed of bone, or an artificial material other than bone which may be harder or stronger than bone, such as, e.g., ceramic materials. Outer housing 510 may include a bone growth promoting material such as, e.g., bone morphogenic protein and hydroxyapatite. Outer housing 510 may define a cavity 551 to accommodate bone graft material therein.

Figure 5A:
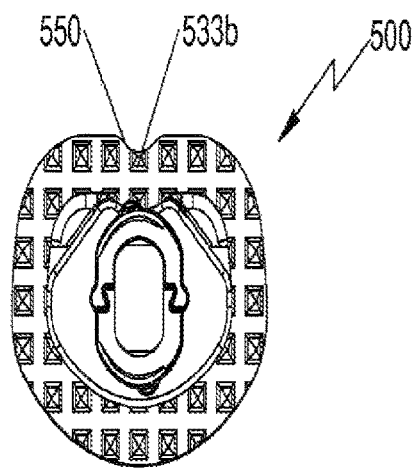
FIG. 5A is a bottom view of the spinal fixation device of FIG. 1.
Figure 5B:
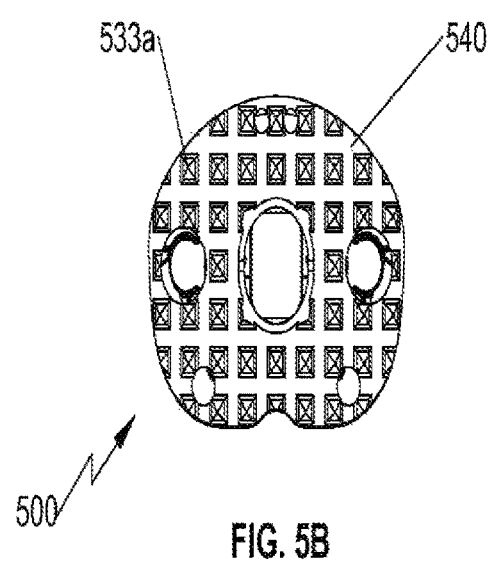
FIG. 5B is a top view of the spinal fixation device of FIG. 1.
Figure 6:
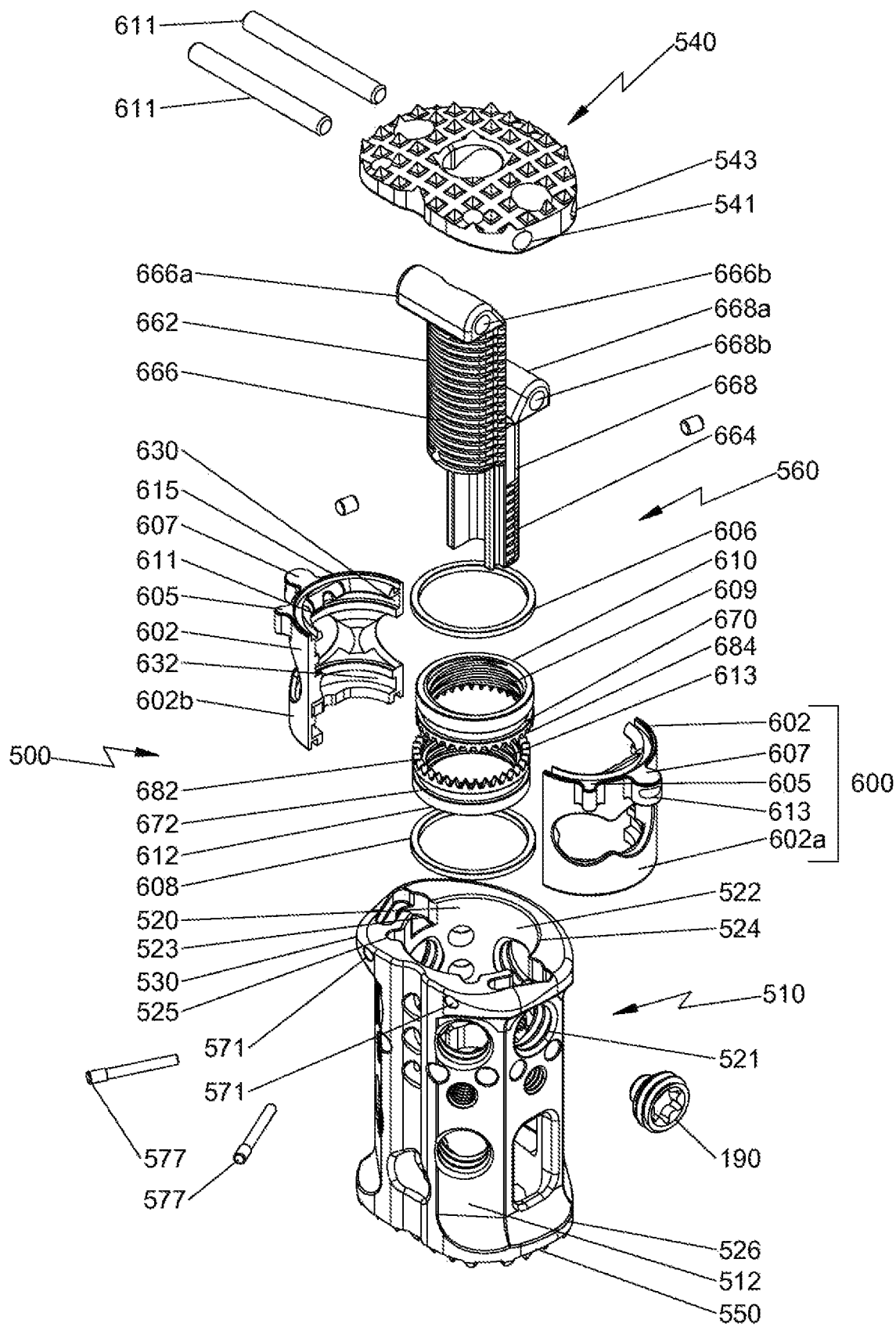
FIG. 6 is a exploded, perspective view of the spinal fixation device of FIG. 1 with parts separated.
Figure 20A:
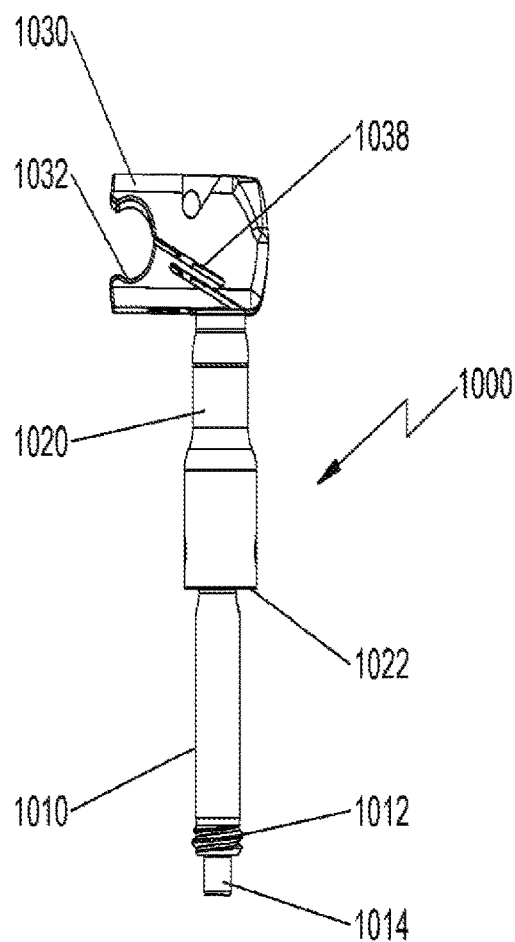
FIG. 20a is a perspective view of a rod connector for use with the spinal fixation device of FIG. 1.

With reference to FIGS. 5A, 5B, and 6, outer housing 510 includes first and second ends 524, 526 and an outer wall 512 extending between first and second ends 524, 526. Outer wall 512 defines a plurality of bores 521 configured to receive a screw 190 and operatively engage insertion instrument 6000 (FIG. 10), as will be discussed hereinbelow. Bores 521 are circumferentially arranged about outer housing 510 to facilitate insertion of screw 190 and engagement with insertion instrument 6000 at different orientations. In addition, outer wall 512 further defines a plurality of bores 527 (FIGS. 7 and 8) circumferentially arranged about outer housing 510 to facilitate fixation of spinal stabilization devices such as, e.g., a rod connector 1000 (FIGS. 20a and 20b), or a drug delivery assembly 1700 (FIG. 25), as will be discussed hereinbelow. For example, the plurality of bores 527 may be defined in anterolateral portions of outer housing 510.

With particular reference to FIGS. 6-9, first end 524 of outer housing 510 defines an aperture 522, and second end 526 of outer housing 510 includes second end plate 550, e.g., integrally formed, with outer housing 510. Outer housing 510 defines a chamber 520 configured to receive at least a portion of end plate assembly 560 through aperture 522. End plate assembly 560 is selectively positionable within chamber 520. End plate assembly 560 includes a mounting assembly 600 releasably supported on a shoulder 530 of first end 524 of outer housing 510. Mounting assembly 600 includes a retaining housing 602 including first and second housing halves 602a, 602b, first and second rotatable members 610, 612 rotatably supported in retaining housing 602, and first and second retaining rings 606, 608.

Figure 7:
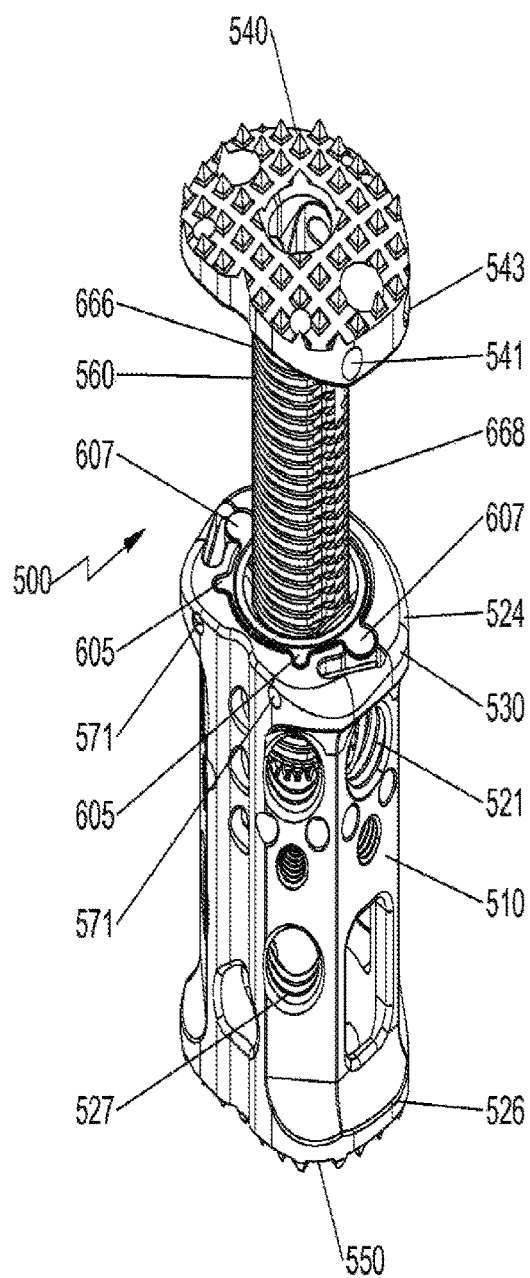
FIG. 7 is a perspective view of the spinal fixation device of FIG. 1 with a first end plate spaced apart from a body of the spinal fixation device.

With particular reference to FIGS. 6 and 7, aperture 522 of first end 524 of outer housing 510 includes a non-circular cross-section complementary to a transverse cross-section of a first end 615 of retaining housing 602 to inhibit rotation of retaining housing 602 in aperture 522. In particular, each of first and second housing halves 602a, 602b includes radially extending first and second protrusions 605, 607 configured to be received in respective first and second recesses 523, 525 defined in shoulder 530 of outer housing 510. Outer housing 510 defines a pair of bores 571 transverse to a longitudinal axis "A" (FIG. 9) of spinal fixation device 500. Each bore 571 is configured to receive a spring pin 577. Each of first and second housing halves 602a, 602b defines a transverse groove 613 on respective second protrusions 607. Transverse groove 613 is configured to receive spring pin 577. Under such a configuration, spring pin 577 inserted through the respective bore 571 of outer housing 510 is received through transverse groove 613 of the respective second protrusion 607 to secure retaining housing 602 with outer housing 510. Spring pin 577 is flexible to enable the clinician to remove end plate assembly 560 from outer body 510 when end plate assembly 560 is pulled away from outer housing 510. When end plate assembly 560 is pulled away from outer housing 510, spring pin 577 flexes and disengages from transverse groove 613 of second protrusion 607. In this manner, the clinician is able to interchangeably utilize various end plate assemblies 560.

With continued reference to FIG. 6, each of first and second housing halves 602a, 602b includes an inner wall 611 defining first and second circumferential grooves 630, 632 configured to receive at least a portion of first and second retaining rings 606, 608, respectively. First rotatable member 610 defines a circumferential groove 670 configured to support first retaining ring 606 therein. First retaining ring 606 extends radially outward from circumferential groove 670 of first rotatable member 610 such that at least a portion of first retaining ring 606 is received in first circumferential groove 630 of retaining housing 602. In this manner, first rotatable member 610 is rotatably supported within retaining housing 602. Similarly, second rotatable member 612 defines a circumferential groove 672 configured to support second retaining ring 608 therein. Second retaining ring 608 extends radially outward from circumferential groove 672 such that at least a portion of second retaining ring 608 is received in second circumferential groove 632 of retaining housing 602. In this manner, second rotatable member 612 is rotatably supported within retaining housing 602. Under such a configuration, first and second rotatable members 610, 612 are rotatable with respect to retaining housing 602, while maintaining a fixed axial distance therebetween.

First and second rotatable members 610, 612 include internal threads 609, 613 (FIG. 6), respectively. In particular, internal threads 609, 613 are in opposite orientations, such that when first and second rotatable members 610, 612 rotate in opposite directions, the orientations of internal threads 609, 613 are the same. Internal threads 609, 613 are configured to threadably engage outer threads 662, 664 of first and second elongate members 666, 668 of end plate assembly 560, respectively. Under such a configuration, rotation of first and second rotatable members 610, 612 in opposite directions causes axial movement of first and second elongate members 666, 668 along longitudinal axis "A-A" (FIG. 9), as will be described hereinbelow. In addition, first and second rotatable members 610, 612 include opposing teeth 682, 684, respectively. Teeth 682, 684 are configured to engage, e.g., an engaging portion 7030 of a height adjusting driver 7000 (FIG. 13A), as will be discussed hereinbelow. Under such a configuration, rotation of height adjusting driver 7000 operatively coupled with teeth 682, 684 causes rotation of first and second rotatable members 610, 612, which, in turn, causes axial movement of first and second elongate members 666, 668.

Figure 8:
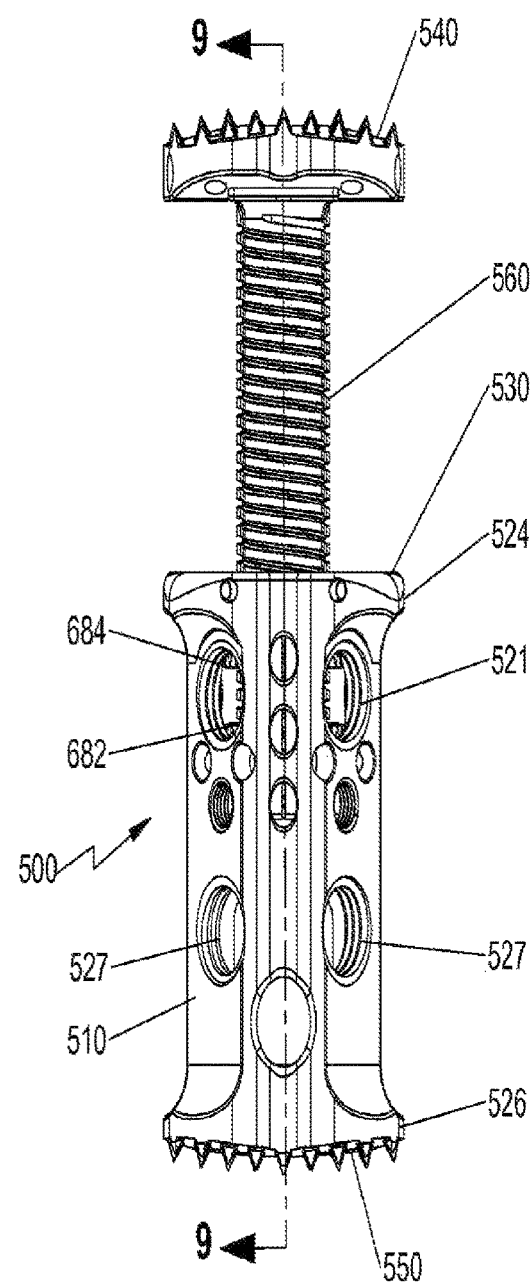
FIG. 8 is a rear view of the spinal fixation device of FIG. 7.
Figure 9:
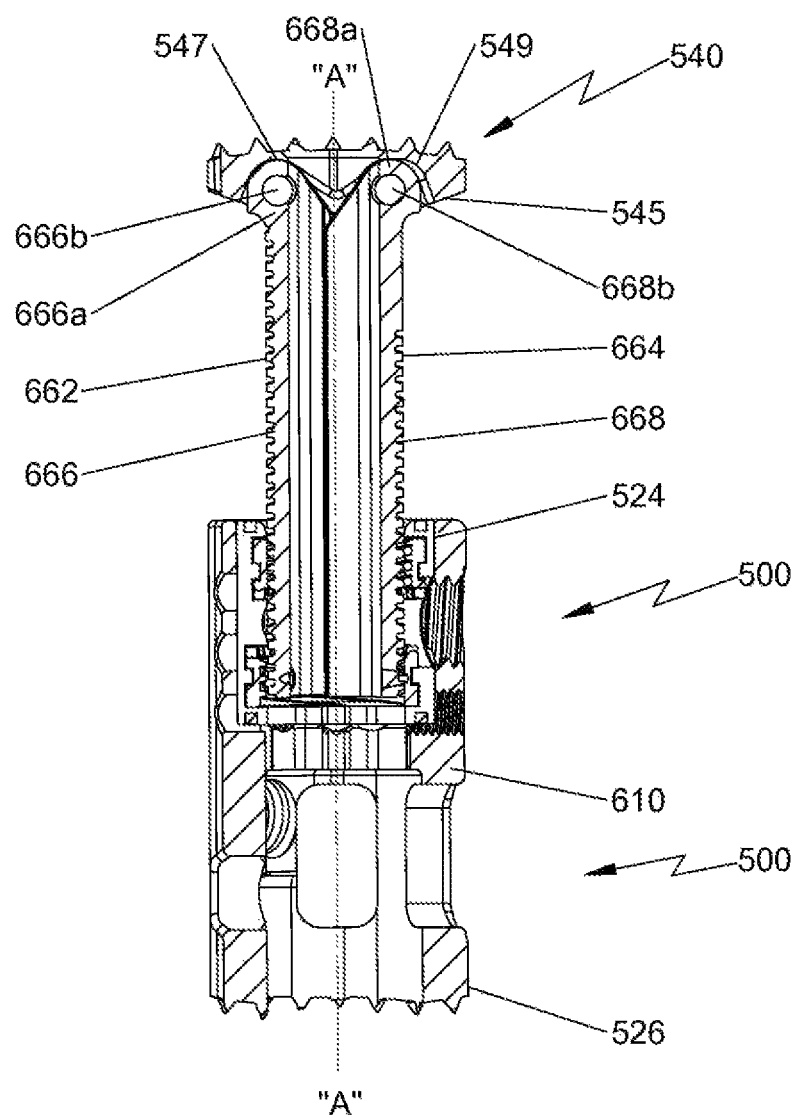
FIG. 9 is a cross-sectional view of the spinal fixation device of FIG. 8 cut along section line "9-9" of FIG. 8.

With continued reference to FIGS. 7-9, end plate assembly 560 is selectively positionable relative to outer housing 510 through rotation of first and second rotatable members 610, 612 in opposite directions. In this manner, a length of spinal fixation device 500 may be selectively tailored to, e.g., the intervertebral space.

With particular reference now to FIG. 9, first end plate 540 includes an underside 545 defining first and second grooves 547, 549. First and second grooves 547, 549 are configured to receive round head portions 666a, 668a of first and second elongate members 666, 668, respectively. Round head portions 666a, 668a define respective bores 666b, 668b. First end plate 540 further defines bores 541, 543 (FIG. 7) configured to receive respective pins 611 (FIG. 6). In this manner, pins 611 pivotably secure round head portions 666a, 668a to first end plate 540. Under such a configuration, relative axial movement of first and second elongate members 666, 668 enables the clinician to adjust angular orientation of first end plate 540 with respect to longitudinal axis "A-A" (FIG. 9) to achieve the desired lordosis, as will be discussed hereinbelow.

First and second elongate members 666, 668 of end plate assembly 560 include outer threads 662, 664 configured to engage internal threads 609, 613 (FIG. 6) of first and second rotatable members 602, 404. First and second elongate members 666, 668 of end plate assembly 560 are movable relative to each other along longitudinal axis "A-A". In this manner, first end plate 540 may be advantageously angled to provide a desired amount of lordosis tailored to the need of each patient. For example, first end plate 540 may be positioned substantially orthogonal to the longitudinal axis "A-A" (FIG. 9) and adjacent first end 524 of outer housing 510. Alternatively, first end plate 540 may define an acute angle with longitudinal axis "A-A" (FIG. 9) and spaced apart from first end 524. The clinician may use angle adjusting driver 8000 to adjust the relative positioning of first and second elongate members 666, 668 to provide the adequate amount of lordosis of first end plate 540, as will be described hereinbelow.

Figure 10:
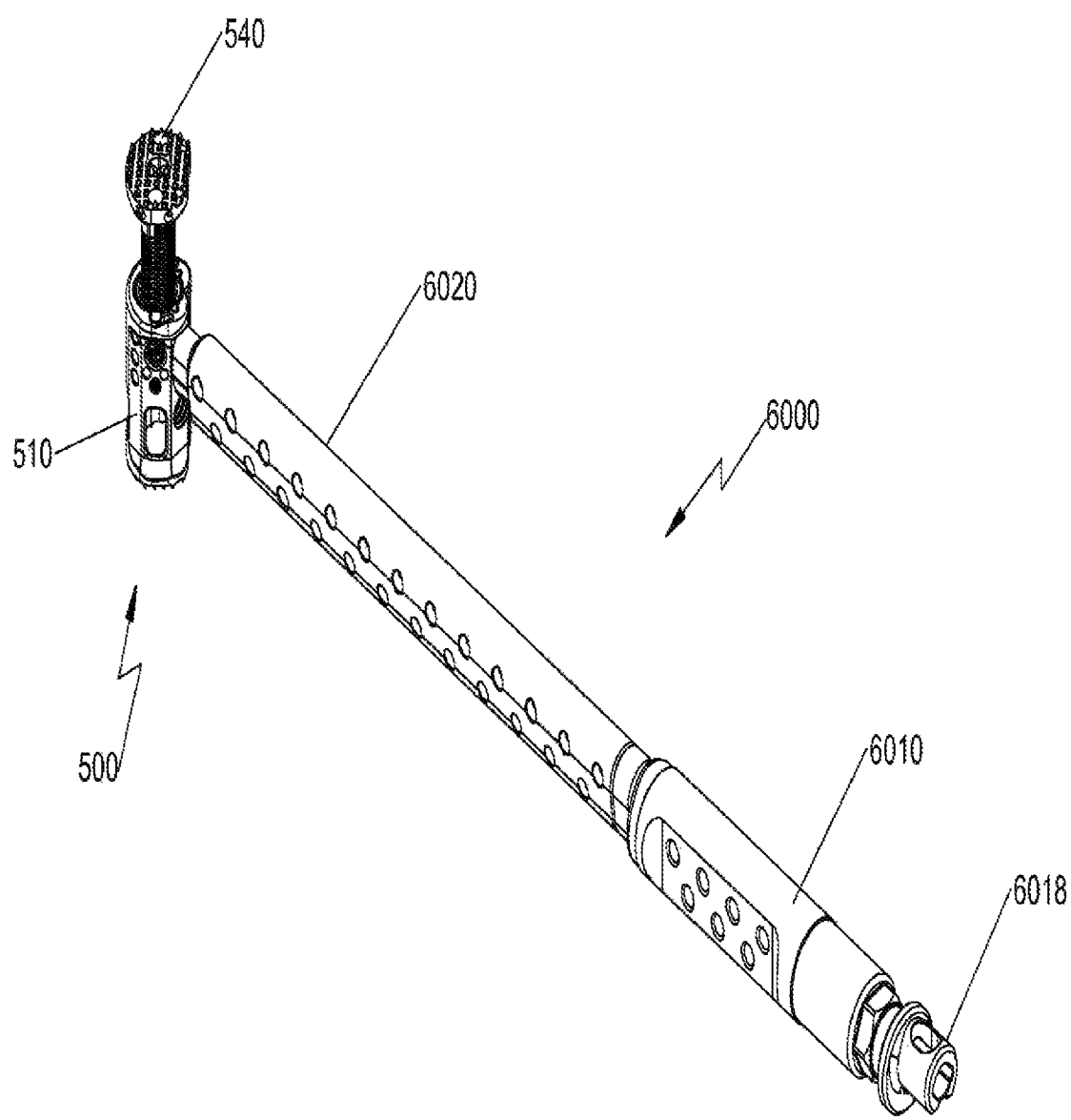
FIG. 10 is a perspective view of an insertion instrument illustrating use with the spinal fixation device of FIG. 1.
Figure 11:
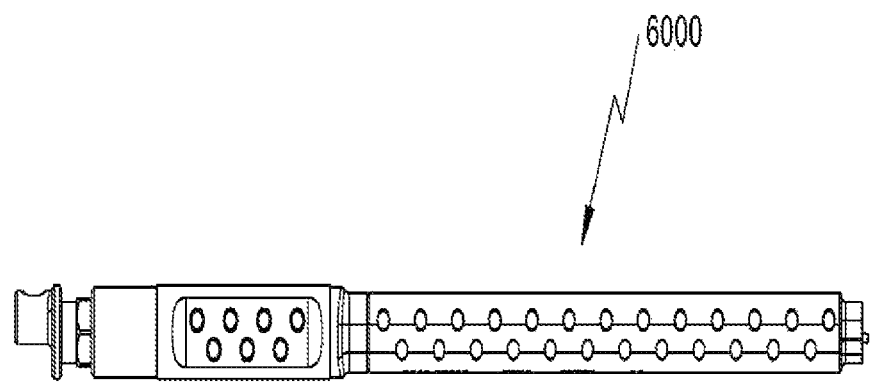
FIG. 11 is a top view of the insertion instrument of FIG. 10.
Figure 12:
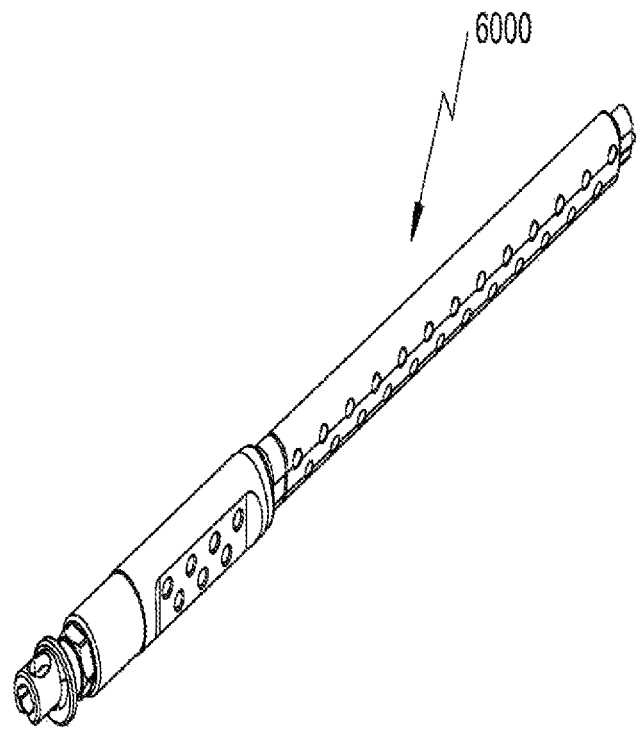
FIG. 12 is a perspective view of the insertion instrument of FIG. 10.
Figure 14:
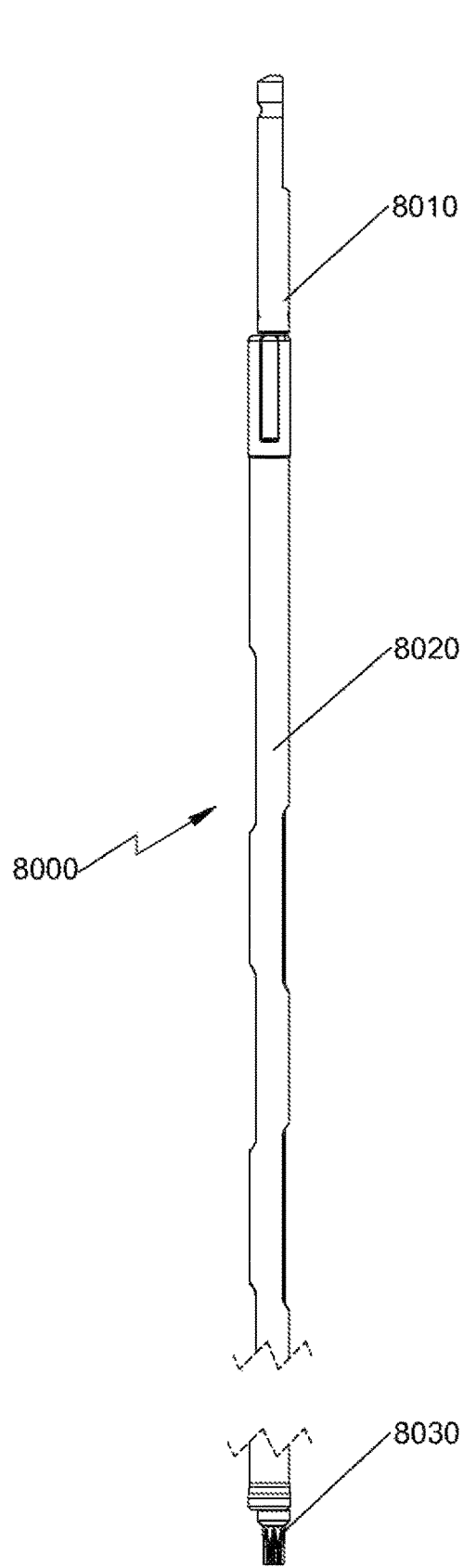
FIG. 14A is a side view of an angle adjusting driver for use with the insertion instrument of FIG. 10.
FIG. 14B is a top view of the angle adjusting driver of FIG. 14A.
FIG. 14C is a partial side view of a distal portion of the angle adjusting driver of FIG. 14A.
Figure 14:
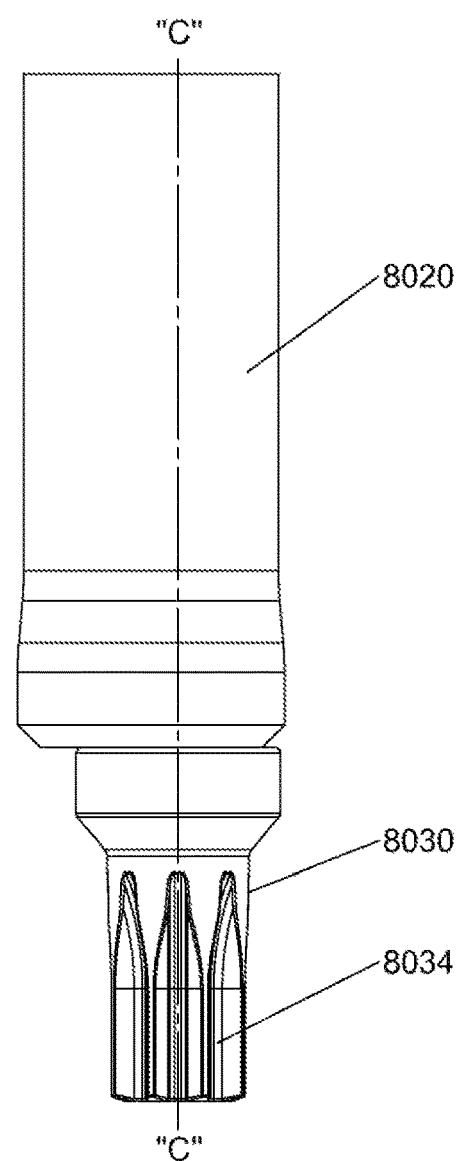
Figure 14:
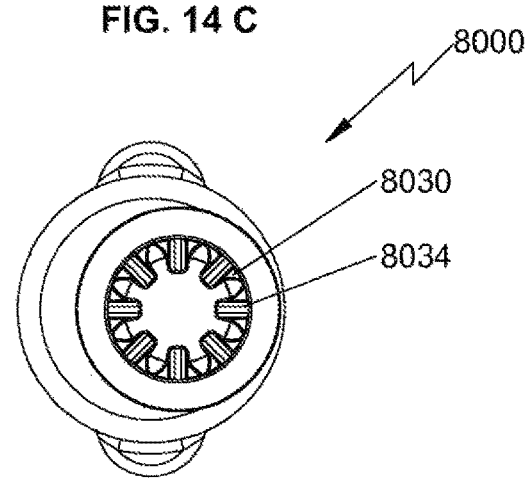
Figure 17:
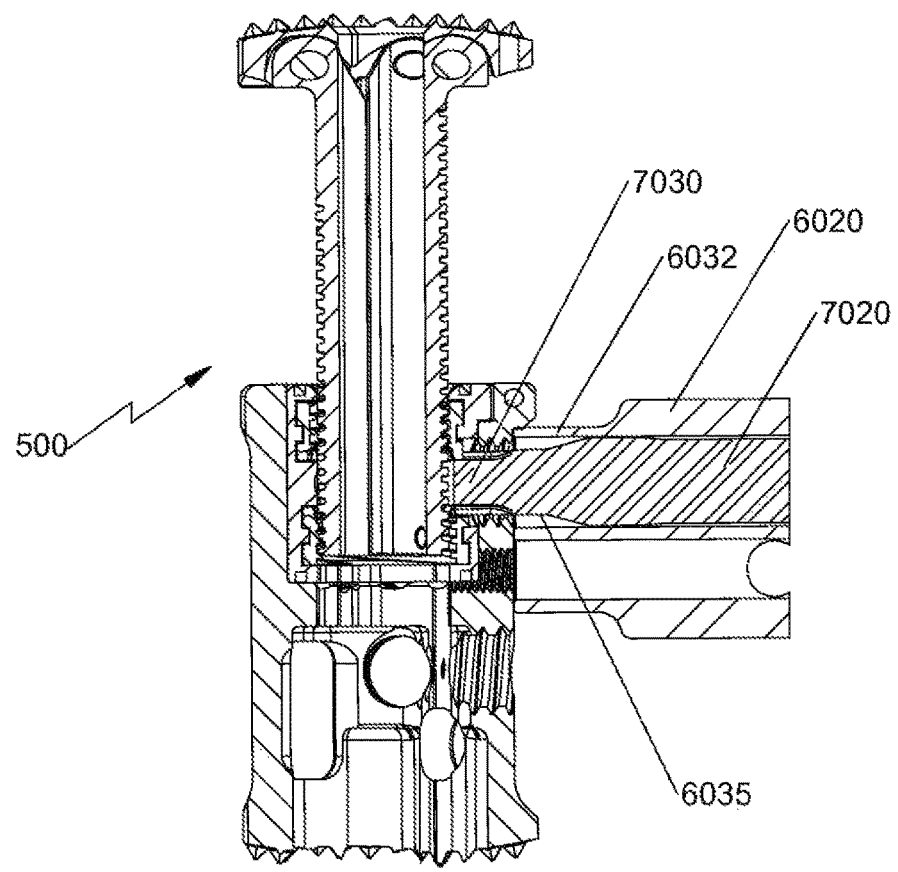
FIG. 17 is a cross-sectional view of the insertion instrument and the spinal fixation device of FIG. 16 cut along section line "17-17" of FIG. 16.
Figure 18:
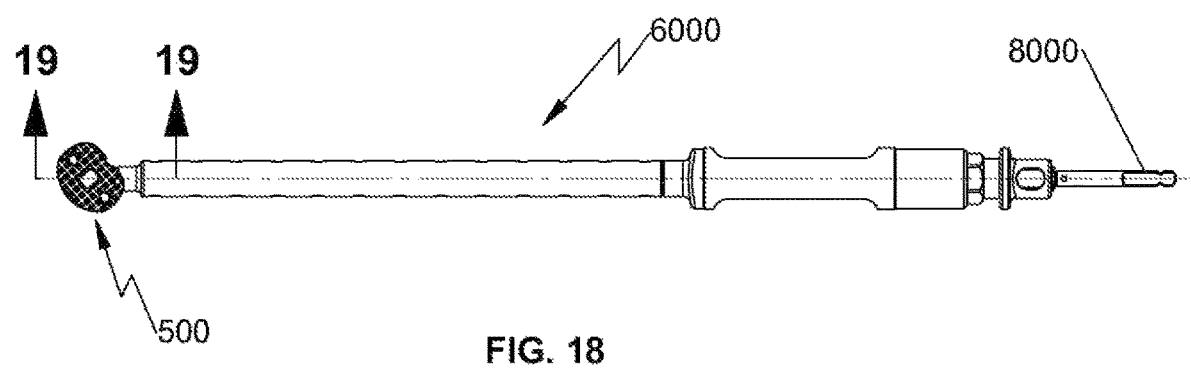
FIG. 18 is a top view of the insertion instrument of FIG. 10 illustrating use with the angle adjusting driver of FIG. 14A and the spinal fixation device of FIG. 1.
Figure 19:
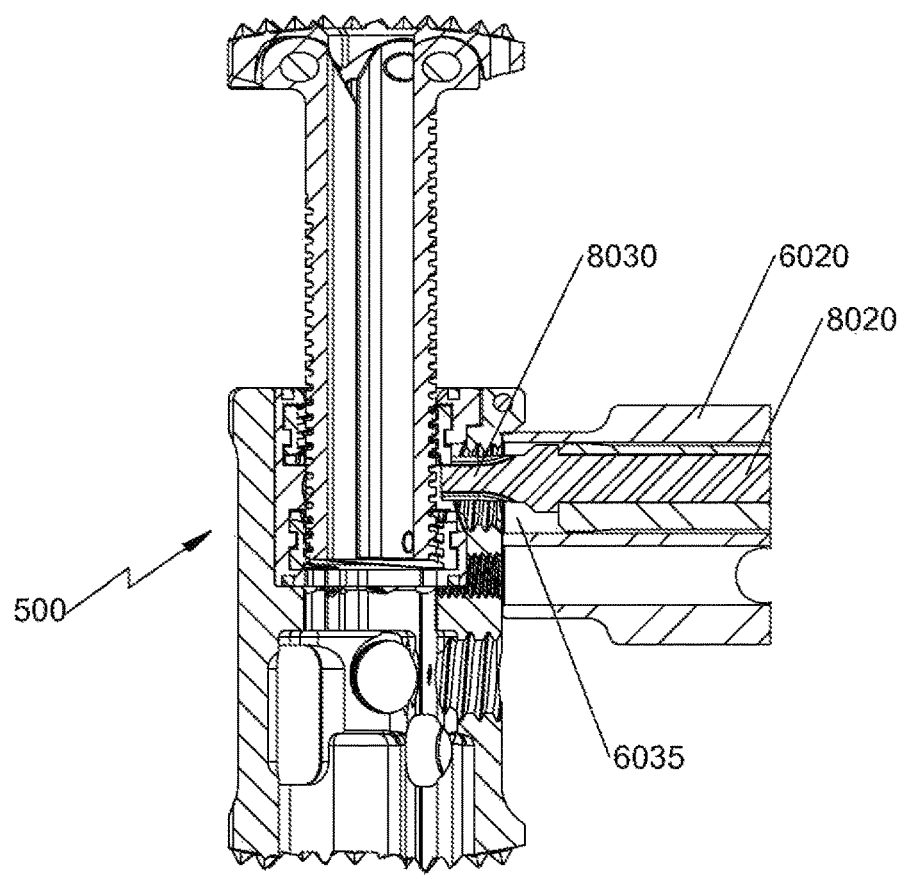
FIG. 19 is a cross-sectional view of the insertion instrument of FIG. 18 cut along section line "19-19" of FIG. 18.

With reference now to FIGS. 10-12, there is shown an insertion instrument 6000 for use with spinal fixation device 500 to position spinal fixation device 500 between adjacent vertebral bodies. Insertion instrument 6000 includes a handle 6010 and an elongate body 6020 extending from handle 6010. Insertion instrument 6000 defines a channel 6035 (FIG. 17) configured to receive a height adjusting driver 7000 (a distal end of height adjusting driver 700 shown in FIG. 17), an angle adjusting driver 8000 (FIG. 18), or a tapered driver 9000 (FIGS. 15A-C) therethrough. Elongate body 6020 includes engaging portion 6032 (FIG. 17) configured to, e.g., threadably, engage bore 521 of outer housing 510 to securely attach spinal fixation device 500 with insertion instrument 6000.

With reference now to FIGS. 13A-C and FIG. 17, there is provided a height adjusting driver 7000 configured to be received through channel 6035 (FIG. 17) of insertion instrument 6000. Height adjusting driver 7000 includes a handle 7010, an elongate body 7020, and an engaging portion 7030. Engaging portion 7030 includes a plurality of teeth 7032 configured to engage teeth 684, 682 (FIG. 6) of first and second rotatable members 610, 612 of mounting assembly 600, respectively. In this manner, rotation of handle 7010 causes concomitant rotation of engaging portion 7030 about elongate body 7020, which, in turn, causes rotation of first and second rotatable members 610, 612 in opposite directions. Rotation of first and second rotatable members 610, 612 in opposite directions imparts axial translation of first and second elongate members 666, 668 as a single construct, which, in turn, enables the clinician to adjust the axial distance between first end plate 540 and outer housing 510, i.e., overall height of spinal fixation device 500. Rotation of handle 7010 in an opposite direction causes axial movement of end plate assembly 560 in an opposite direction.

With reference now to FIGS. 14A-C and 19, there is provided an angle adjusting driver 8000 configured to be received through channel 6035 (FIG. 17) of insertion instrument 6000. Angle adjusting driver 8000 includes a handle 8010, an elongate body 8020, and an engaging portion 8030. For example, engaging portion 8030 may be radially offset from a central axis "C-C" defined by elongate body 8020. Engaging portion 8030 includes a plurality of teeth 8034 configured to engage teeth 682, 684 (FIG. 6) of either first or second rotatable members 610, 612 of mounting assembly 600. In this manner, rotation of handle 8010 causes rotation of one of the first or second rotatable members 610, 612 of mounting assembly 600. Rotation of only one rotatable member 610, 612 causes translation of one of first or second elongate member 666, 668. Relative movement between first and second elongate members 666, 668 changes angular orientation of first end plate 540 with respect to outer housing 510 and longitudinal axis "A-A." In this manner, the clinician may adjust the angular orientation of first end plate 540 to achieve the desired amount of lordosis or kyphosis. It is also contemplated that height adjusting driver 7000 and angle adjusting driver 8000 may be constructed as a single instrument that is configured to be received through channel 6035 (FIG. 17) of insertion instrument 6000.

With reference now to FIGS. 15A-C, there is provided a tapered driver 9000 configured to be received through channel 6035 (FIG. 17) of insertion instrument 6000. Tapered driver 9000 includes a handle 9010, an elongate body 9020, and an engaging portion 9030. Upon achieving the desired height of spinal fixation device 500 using height adjusting driver 7000 and angular orientation of first end plate 540 using angle adjusting driver 8000, screws 190 may be positioned in bore 521 of outer housing 510 through channel 6035 of insertion instrument 6000. Teeth 9034 of engaging portion 9030 engage teeth on a head portion of screw 190. Under such a configuration, handle 9010 may be rotated to threadably secure screw 190 in bore 521.

Figure 20B:
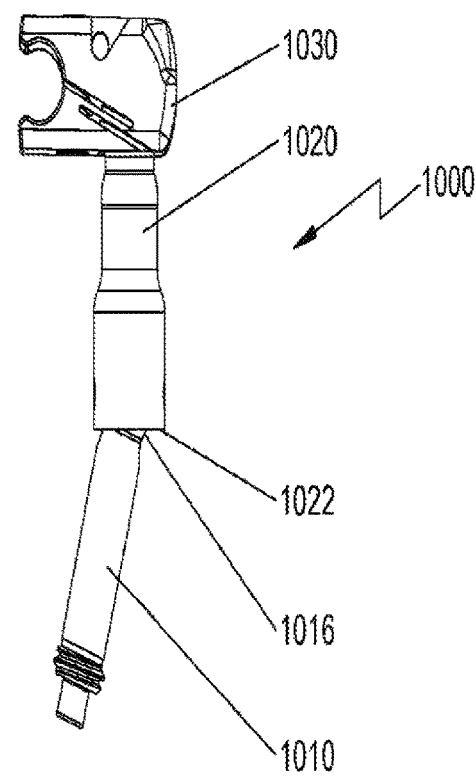
FIG. 20b is a perspective view of the rod connector of FIG. 20a illustrating polyaxial rotation thereof.
Figures 21A, 21B:
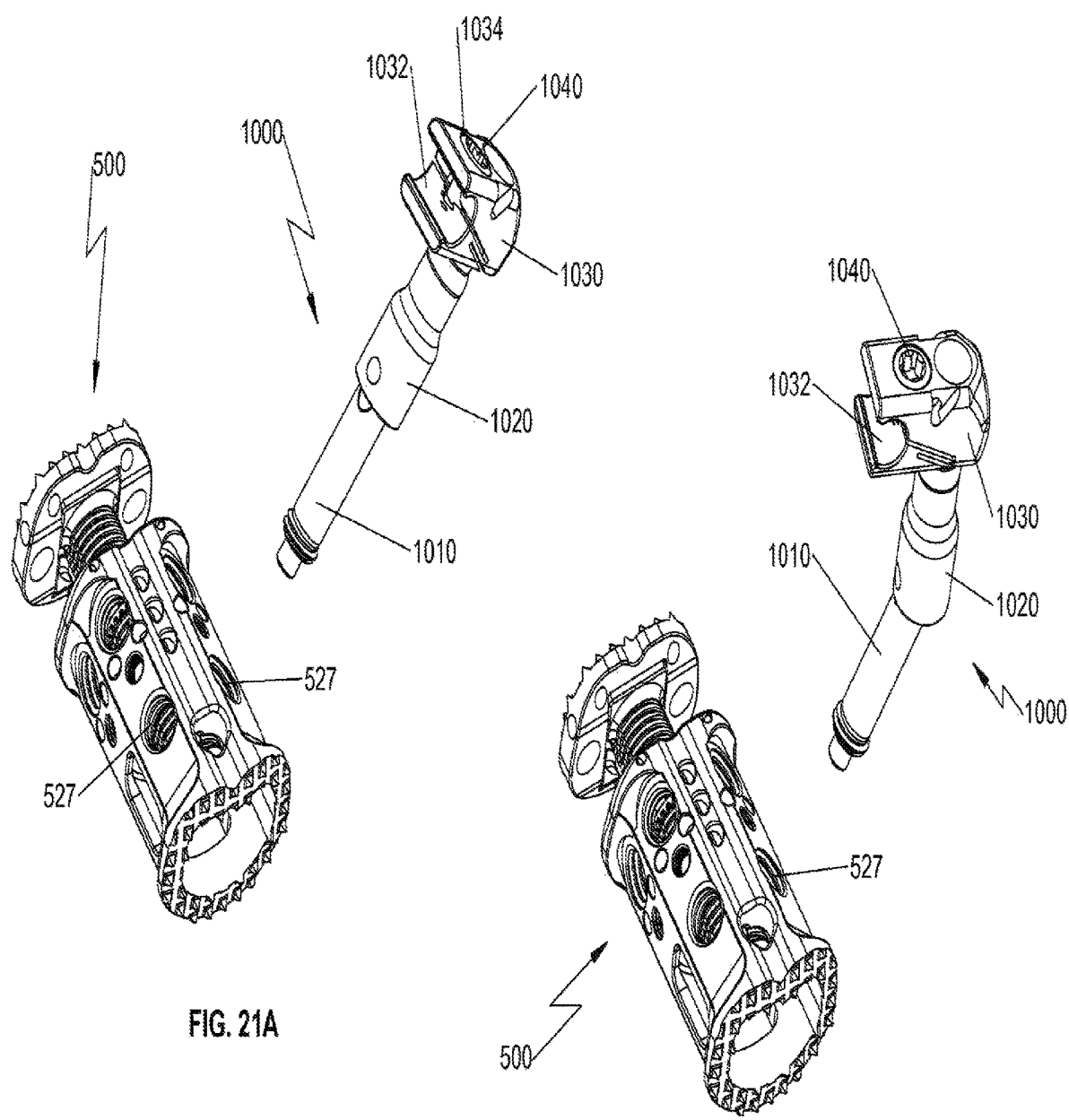

With reference now to FIGS. 20-21, a rod connector 1000 and a spinal rod 1500 (FIG. 22) may be used with spinal fixation device 500 to enhance securement of spinal fixation device 500 between vertebral bodies and to promote spinal fusion. Rod connector 1000 includes an anchoring portion 1010, a coupling portion 1020 rotatably and pivotably coupled with anchoring portion 1010, and a head portion 1030. Anchoring portion 1010 includes an engaging portion 1012 configured to be threadably coupled with bore 527 (FIGS. 21a and 21b) of spinal fixation device 500. Anchoring portion 1010 further includes a tip portion 1014 extending from engaging portion 1012. Tip portion 1014 has a diameter smaller than a diameter of engaging portion 1012 to facilitate alignment of engaging portion 1012 with bore 527. Anchoring portion 1010 further includes a ball joint 1016 (FIG. 20b). Coupling portion 1020 includes a socket 1022 configured to rotatably and pivotably receive ball joint 1016 of anchoring portion 1010. Under such a configuration, variable or polyaxial adjustments may be made between anchoring portion 1010 and coupling portion 1020. It is also contemplated that anchoring portion 1010 may include a socket and coupling portion 1020 may include a ball joint.

Figure 22:
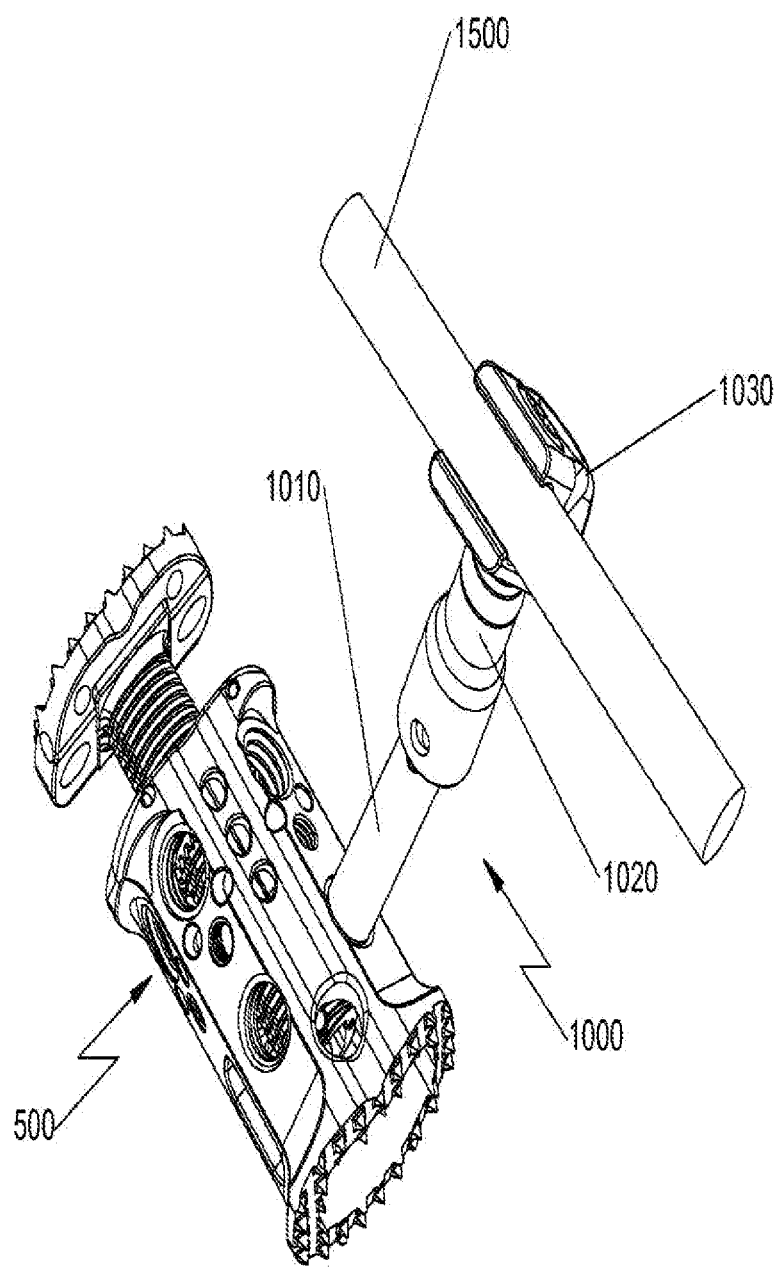
FIG. 22 is a perspective view of the spinal fixation device and the rod connector of FIG. 21a secured with the spinal fixation device illustrating use with a spinal rod.

With reference to FIGS. 20-22, coupling portion 1020 is secured with head portion 1030. Head portion 1030 includes a recessed portion 1032 configured to receive spinal rod 1500 therethrough. Head portion 1030 defines slits 1038 configured to flex or enlarge the dimensions of recessed portion 1032 to facilitate insertion of spinal rod 1500. Head portion 1030 further defines a bore 1034 (FIG. 21a) configured to receive a screw 1040. Upon insertion of spinal rod 1500 in recessed portion 1032, screw 1040 may be fastened to secure spinal rod 1500 in recessed portion 1032. With particular reference to FIG. 22, spinal rod 1500 may be, e.g., a 5.5 mm diameter round rod. A reference may be made to U.S. patent application Ser. No. 13/251,546, now U.S. Pat. No. 8,920,471, filed on Oct. 3, 2011, entitled "Transverse Connector," the entire content of which is incorporated herein by reference, for a detailed discussion of the construction and operation of screws.

Figure 23:
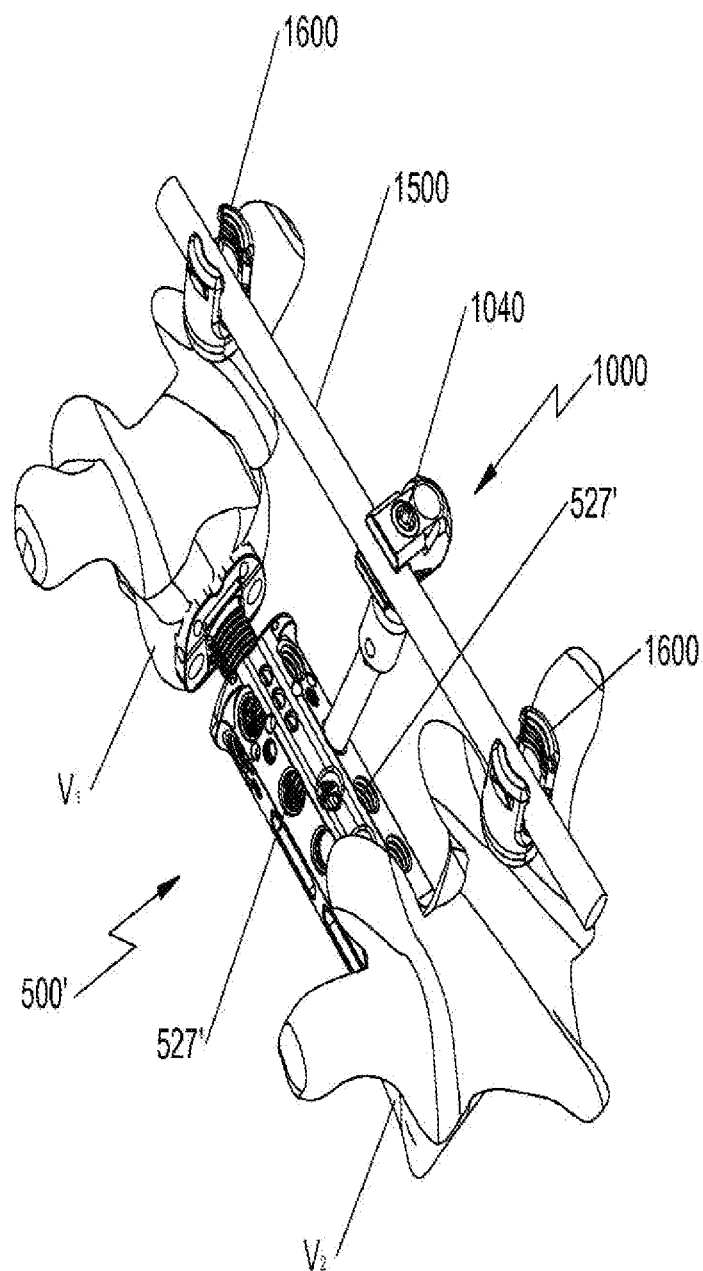
FIG. 23 is a perspective view of the spinal fixation device of FIG. 22 secured between vertebral bodies by the rod connector and the spinal rod of FIG. 22.

With reference now to FIG. 23, it is also envisioned that spinal fixation device 500 may be tailored to a particular surgical procedure being performed. For example, spinal fixation device 500' may include a plurality of bores 527' axially arranged along a length of spinal fixation device 500'. Under such a configuration, rod connector 1000 may be secured at a desired location along the length of spinal fixation device 500 to better secure spinal fixation device 500' between vertebral bodies $v_1$, $v_2$. In addition, it is also contemplated that additional rod connectors 1000 may be axially placed along the length of spinal fixation device 500' to further secure spinal fixation device 500'. In this manner, after spinal fixation device 500' is positioned between vertebral bodies $v_1$, $v_2$, pedicle screws 1600 may be secured to respective vertebral bodies $v_1$, $v_2$ and at least one rod connector 1000 may be secured with spinal fixation device 500'. Spinal rod 1500 may be received through the pedicle screws and rod connector 1000. Screw 1040 is utilized to secure spinal rod 1500 in recessed portion 1032 of rod connector 1000 and set screws (not shown) are used to secure spinal rod 1500 with pedicle screws 1600. A reference may be made to U.S. patent application Ser. No. 12/739,461, now U.S. Pat. No. 8,814,919, filed on Aug. 26, 2014, entitled "Posterior Pedicle Screw Having a Taper Lock," and Ser. No. 12/739,506, filed on Oct. 22, 2008, entitled "Polyaxial Screw Assembly," the entire content of each of which is incorporated herein by reference, for a detailed discussion of the construction and operation of spinal rods and rod connectors.

Figure 24:
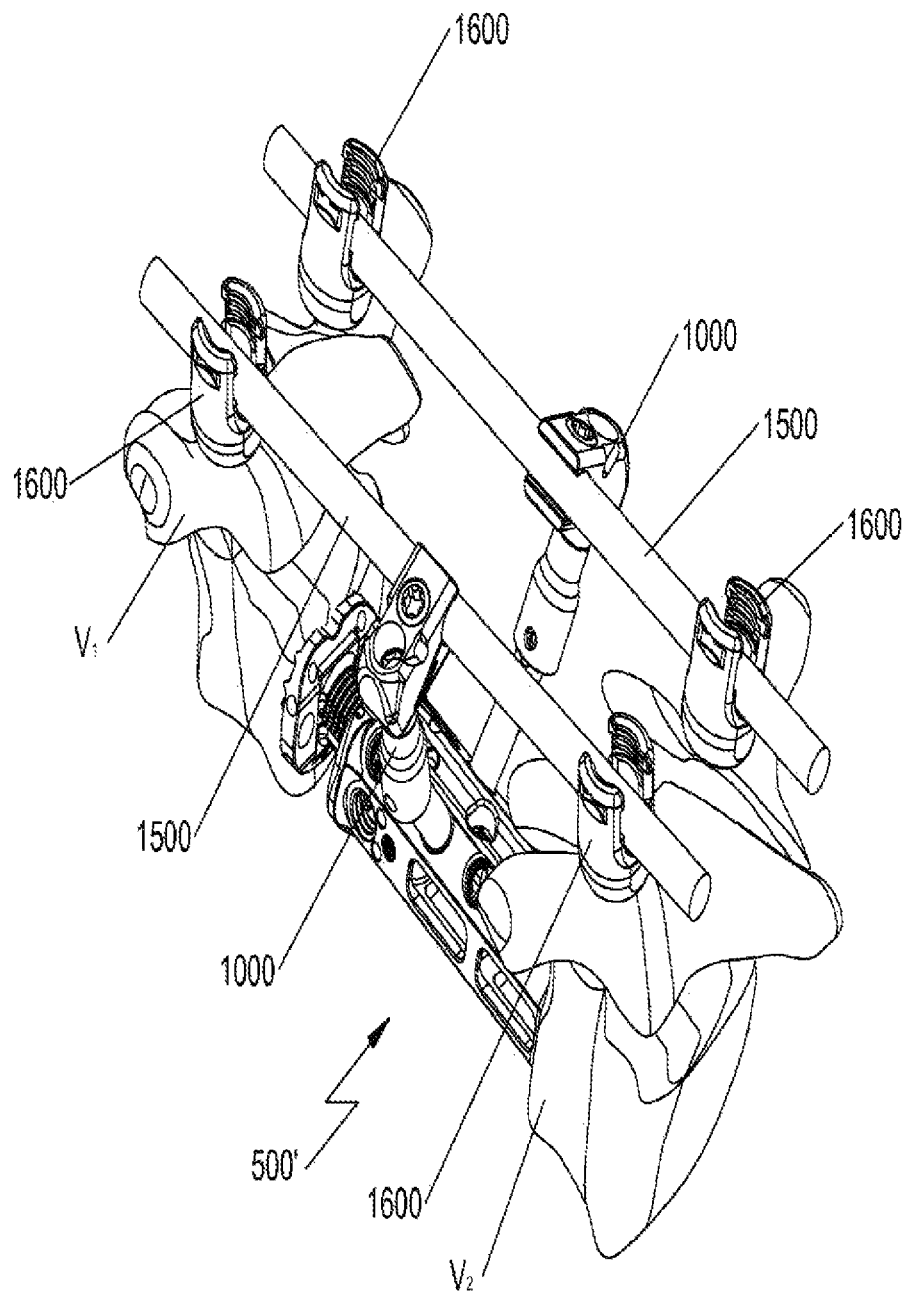
FIG. 24 is a perspective view of the spinal fixation device of FIG. 22 secured between the vertebral bodies by a pair of rod connectors and spinal rods of FIG. 22.

With reference to FIG. 24, it is also envisioned that a pair of spinal rods 1500 may be utilized to further secure spinal fixation device 500' between vertebral bodies $v_1$, $v_2$. As discussed hereinabove, additional rod connectors 1000 may be axially placed along the length of spinal fixation device 500'.

Figure 25:
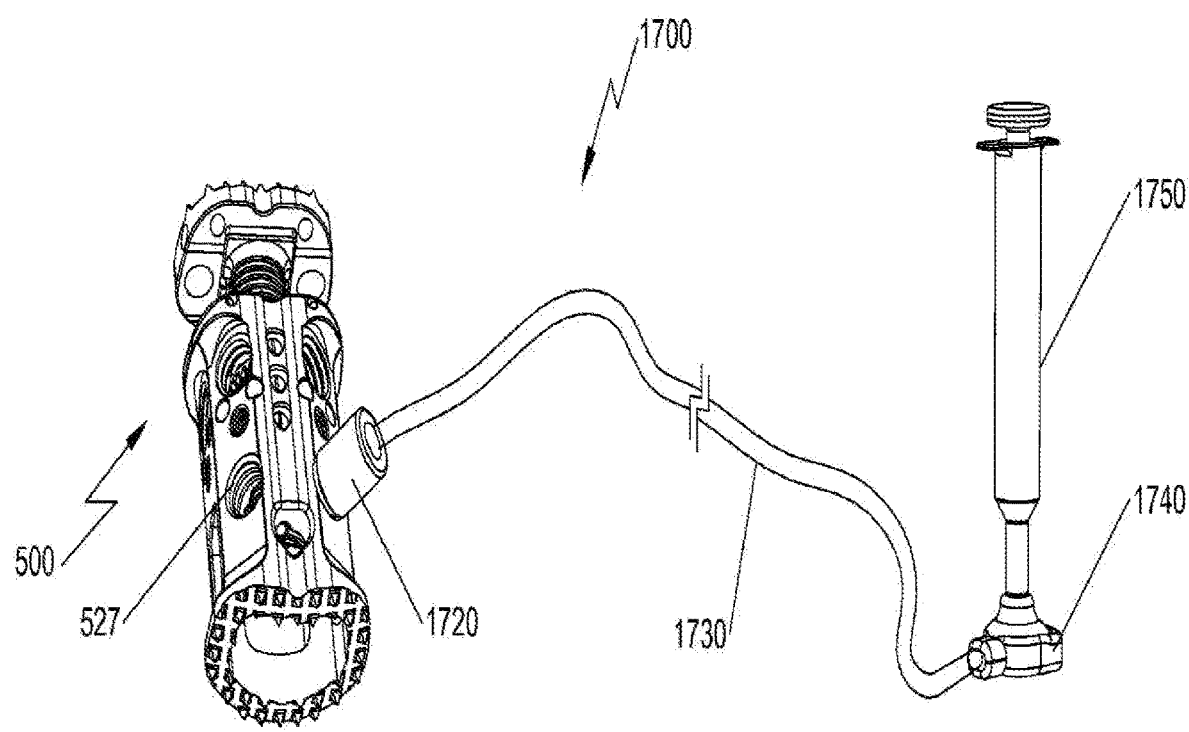
FIG. 25 is a perspective view of the spinal fixation device of FIG. 1 and a drug delivery assembly operatively coupled with the spinal fixation device.

With reference now to FIG. 25, bores 527 may also be used to secure a drug delivery assembly 1700 to deliver a range of different synthetic or naturally occurring pharmaceutical or biological agents in liquid or gel formulations depending upon the particular application. Drugs may be administered for any actual or potential therapeutic, prophylactic or other medicinal purpose. Such drugs may include, e.g., analgesics, anesthetics, antimicrobial agents, antibodies, anticoagulants, antifibrinolytic agents, anti-inflammatory agents, antiparasitic agents, antiviral agents, cytokines, cytotoxins or cell proliferation inhibiting agents, chemotherapeutic agents, radiolabeled compounds or biologics, hormones, interferons, and combinations thereof. Thus, it is contemplated that spinal fixation device 500 may be used to deliver a formulation comprising an agent used in chemotherapy or radiotherapy.

Therapeutic agents may include chemotherapeutic agents (for example, paclitaxel, vincristine, ifosfamide, dacttinomycin, doxorubicin, cyclophosphamide, and the like), bisphosphonates (for example, alendronate, pamidronate, clodronate, zoledronic acid, and ibandronic acid), analgesics (such as opioids and NSAIDS), anesthetics (for example, ketoamine, bupivacaine and ropivacaine), tramadol, and dexamethasone. In other variations, drug delivery assembly 1700 may be used for delivering an agent useful in radiotherapy in, e.g., beads.

As an alternative to systemic administration of radioactive agents that are capable of targeting a particular tissue, antigen, or receptor type, the radioactive agents are administered locally following implantation of spinal fixation device 500. Such radiotherapy agents include radiolabeled antibodies, radiolabeled peptide receptor ligands, or any other radiolabeled compound capable of specifically binding to the specific targeted cancer cells.

In addition, drug delivery assembly 1700 may be used to deliver drugs used in the management of pain and swelling that occurs following the implantation surgery. For example, spinal fixation device 500 may release an effective amount of an analgesic agent alone or in combination with an anesthetic agent. As yet another alternative, spinal fixation device 500 may be used to deliver drugs which help minimize the risk of infection following implantation. For example, spinal fixation device 500 may release one or more antibiotics (for example, cefazolin, cephalosporin, tobramycin, gentamycin, etc.) and/or another agent effective in preventing or mitigating biofilms (for example, a quorum-sensing blocker or other agent targeting biofilm integrity). Bacteria may form biofilms on the surface of spinal fixation device 500, and these biofilms may be relatively impermeable to antibiotics. Accordingly, systemically administered antibiotics may not achieve optimal dosing where it is most needed. However, spinal fixation device 500 enables the delivery of the desired dose of antibiotic precisely when and where needed. In certain circumstances, the antibiotic may be delivered beneath the biofilm.

With reference to FIG. 25, drug delivery assembly 1700 includes a drug reservoir 1720 secured with bore 527, a catheter 1730 in fluid communication with drug reservoir 1720, and a supply port 1740 in fluid communication with catheter 1730. Supply port 1740 may be affixed to a location most convenient for the patient or the clinician to supply the drugs using, e.g., syringe 1750. For example, supply port 1740 may be affixed to an external location such as, e.g., the skin, of the patient. Supply port 1740 shown herein is merely exemplary and not drawn to scale. Supply port 1740 having different sizes, shapes, or profiles may be utilized for other applications such as, e.g., subcutaneous application.

The drugs discussed hereinabove, may be supplied through supply port 1740 by a syringe 1750. It is also contemplated that drug reservoir 1720 may be preloaded with a predetermined amount of drugs to eliminate catheter 1730, supply port 1740, and syringe 1750. It is further contemplated that spinal fixation device 500 may include channels, pores, and/or passages (not shown) formed in, e.g., outer housing 510. The channels, pores, and/or passages may be in fluid communication with drug reservoir 1720 to facilitate delivery of the drugs from drug reservoir 1720 to the delivery target.

Figure 26:
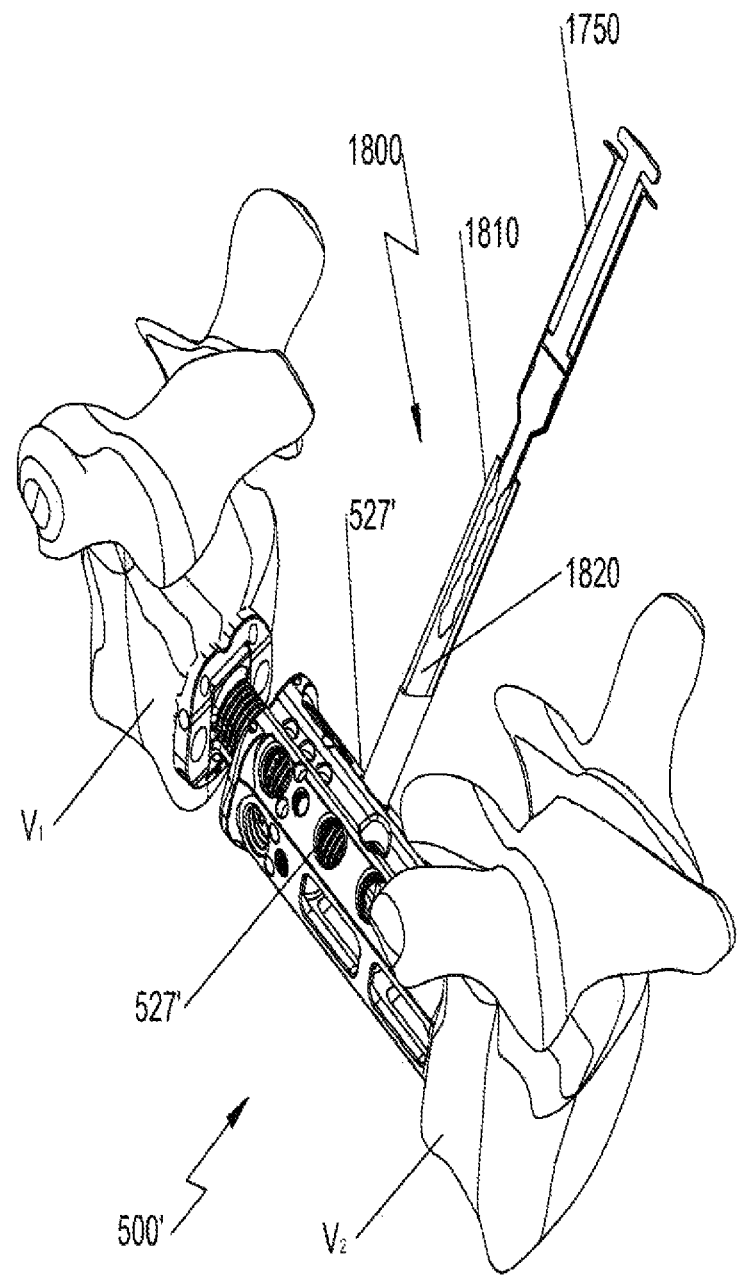
FIG. 26 is a perspective view of the spinal fixation device of FIG. 23 and a drug delivery assembly in accordance with another embodiment of the present disclosure.

With reference to FIG. 26, bores 527' of spinal fixation device 500' or alternatively, bores 527 of spinal fixation device 500, may also be used to secure a drug delivery assembly 1800 to deliver the drugs. Drug delivery assembly 1800 includes a cannula 1810 defining a channel 1820 therethrough. The drugs discussed hereinabove, may be supplied to bores 527, 527' by syringe 1750 coupled to cannula 1810. It is contemplated that cannula 1810 may be coupled to spinal fixation device 500, 500' to supply the drugs to the delivery target during the surgical procedure and may be removed after the completion of the surgical procedure.

Figures 27, 28:
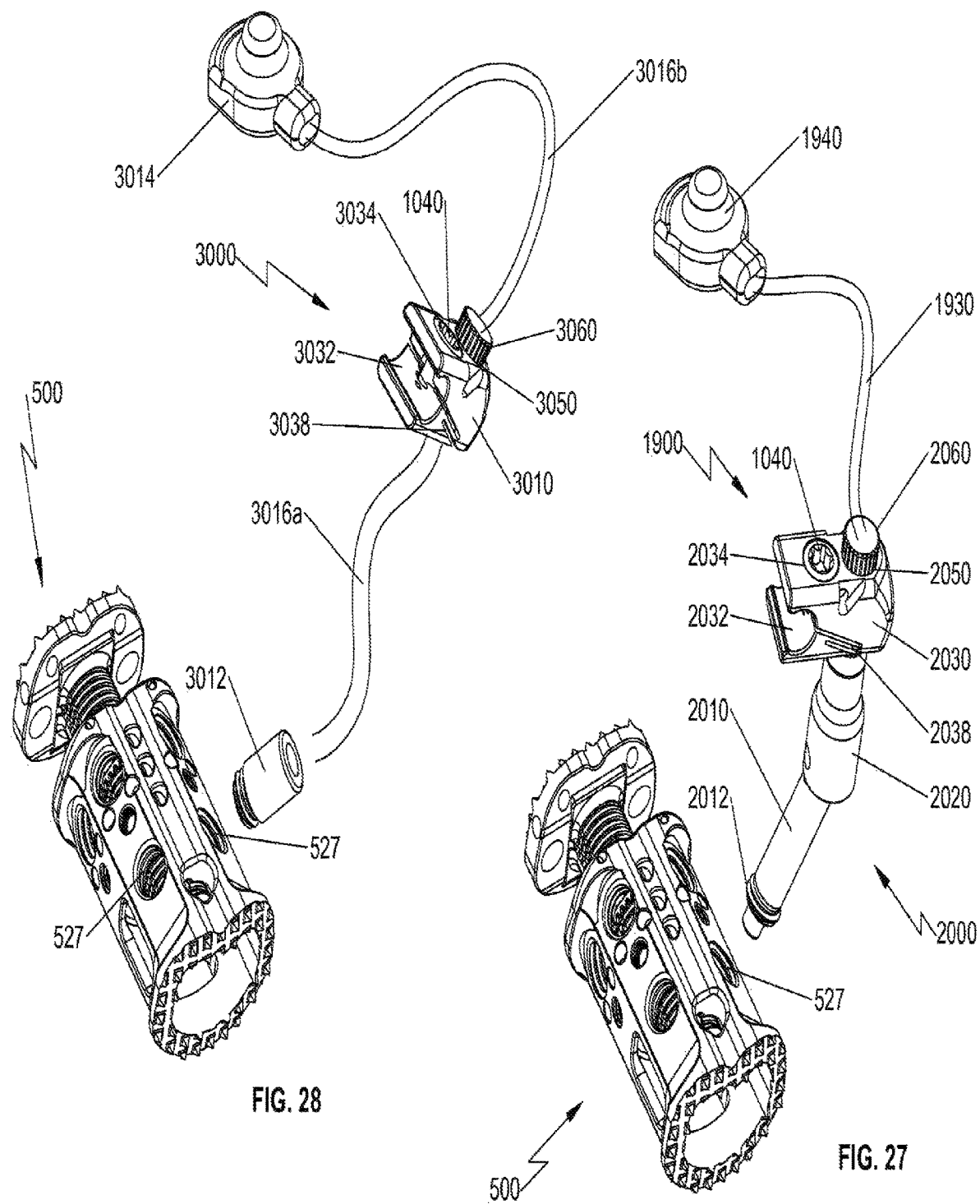
FIG. 27 is a perspective view of the spinal fixation device of FIG. 1 and a drug delivery assembly for use with the spinal fixation device in accordance with another embodiment of the present disclosure.
FIG. 28 is a perspective view of the spinal fixation device of FIG. 1 and a drug delivery assembly for use with the spinal fixation device in accordance with an alternative embodiment of the present disclosure.

With reference now to FIG. 27, it is also envisioned that a drug delivery assembly 1900 may be utilized to deliver the drugs to the delivery target. Drug delivery assembly 1900 includes rod connector 2000, a seal member 2060, a supply port 1940, and a catheter 1930 interconnecting supply port 1940 and rod connector 2000. In particular, rod connector 2000 defines a channel (not shown) extending therethrough such that when rod connector 2000 is coupled with spinal fixation device 500, 500', the channel is in fluid communication with bore 527, 527' of spinal fixation device 500, 500' to facilitate drug delivery through rod connector 2000.

Rod connector 2000 has a substantially similar configuration as rod connector 1000. The portions of rod connector 2000 that are identical to rod connector 1000, as discussed hereinabove, will not be discussed in detail. Rod connector 2000 includes an anchoring portion 2010, a coupling portion 2020 rotatably and pivotably coupled with anchoring portion 2010, and a head portion 2030. Anchoring portion 2010 includes an engaging portion 2012 configured to be threadably coupled with bore 527 of spinal fixation device 500. Coupling portion 2020 is secured with head portion 2030. Head portion 2030 includes a recessed portion 2032 configured to receive spinal rod 1500 therethrough. Head portion 2030 defines slits 2038 configured to flex or enlarge the dimensions of recessed portion 2032 to facilitate insertion of spinal rod 1500. Head portion 1030 further defines a bore 2034 configured to receive screw 1040. Upon insertion of spinal rod 1500 in recessed portion 2032, screw 1040 may be fastened to secure spinal rod 1500 in recessed portion 2032. Furthermore, head portion 2030 defines a bore 2050 in communication with the channel. Bore 2050 is dimensioned to receive seal member 2060 in a sealing relation. Under such a configuration, when the patient or the clinician supplies the drugs through supply port 1940 using, e.g., syringe 1750 (FIG. 25), the drugs flow through the channel of rod connector 2000 and to the drug delivery target through bore 527, 527' of spinal fixation device 500, 500'. Alternatively, rod connector 2000 may include a drug reservoir preloaded with a predetermined amount of drugs such that catheter 1930, supply port 1940, and seal member 2060 may be eliminated. Under such a configuration, a plug may be used to close bore 2050 in communication with the channel. In this manner, rod connector 2000 may provide, e.g., time-release, drug delivery.

With reference now to FIG. 28, it is also envisioned that a drug delivery assembly 3000 may be utilized to deliver the drugs to the delivery target. In particular, drug delivery assembly 3000 includes a rod connector 3010, an engaging portion 3012, a seal member 3060, a supply port 3014, and catheters 3016a, 3016b. Rod connector 3010 is substantially identical to head portion 2030 of drug delivery assembly 1900, and thus, will not be described in detail herein. Rod connector 3010 includes a recessed portion 3032 configured to receive spinal rod 1500 therethrough. Rod connector 3010 defines slits 3038 configured to flex or enlarge the dimensions of recessed portion 3032 to facilitate insertion of spinal rod 1500. Rod connector 3010 further defines a bore 3034 configured to receive screw 1040. Upon insertion of spinal rod 1500 in recessed portion 3032, screw 1040 may be fastened to secure spinal rod 1500 in recessed portion 3032. Furthermore, connecting rod 3010 defines a bore 3050. Bore 3050 is dimensioned to receive seal member 3060 in a sealing relation. Catheter 3016a connects bore 3050 with engaging portion 3012, and catheter 3016b interconnects supply port 3014 with seal member 3060. Engaging portion 3012 may be e.g., threadably, coupled with bore 527, 527' of spinal fixation device 500, 500'. Under such a configuration, when the patient or the clinician supplies the drugs to supply port 3014 using, e.g., syringe 1750 (FIG. 25), the drugs flow through rod connector 3010 and bores 527, 527' of spinal fixation device 500, 500' to the drug delivery target. Alternatively, rod connector 3010 may include a drug reservoir preloaded with a predetermined amount of drugs such that catheter 3016b, supply port 3014, and seal member 3060 are eliminated. Under such a configuration, a plug (not shown) may be used to close bore 3050. In this manner, rod connector 3010 may provide, e.g., time-release, drug delivery.

Figure 29:
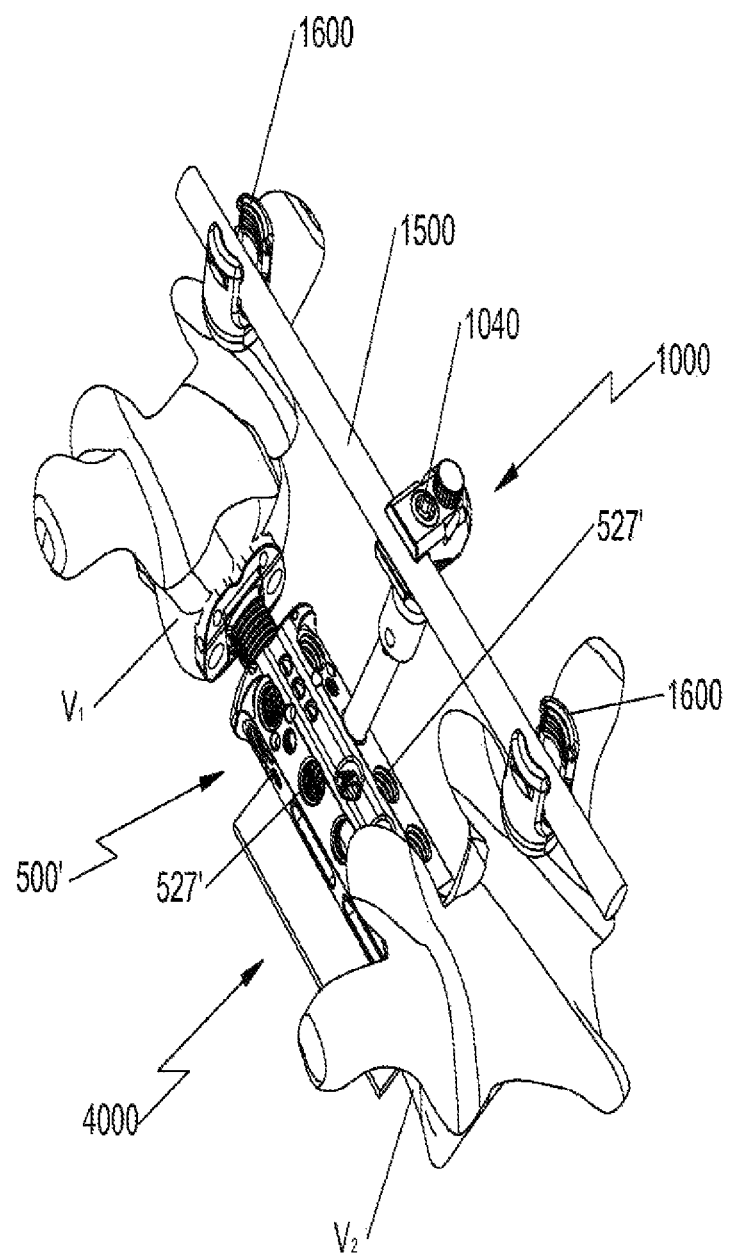
FIG. 29 is a perspective view of the spinal fixation device of FIG. 23 and a shield for use with the spinal fixation device in accordance with an embodiment of the present disclosure, illustrating placement of the shield on the spinal fixation device in phantom.

With reference to FIG. 29, a shield for use with spinal fixation device 500, 500' is generally shown as 4000. Shield 4000 may be affixed to spinal fixation device 500, 500' using adhesive, ultrasonic welding or other suitable means. Shield 4000 may include, e.g., polyphenylene sulfide (PPS), to reduce radiation to the spinal cord during, e.g., post-operative radiotherapy. In addition, shield 4000 may serve as a barrier for bone cement such as, e.g., polymethyl methacrylate (PMMA), drugs, or bone graft products and biologics. In addition, shield 4000 may include, e.g., slow release agents such as antibiotics.

Figure 16:
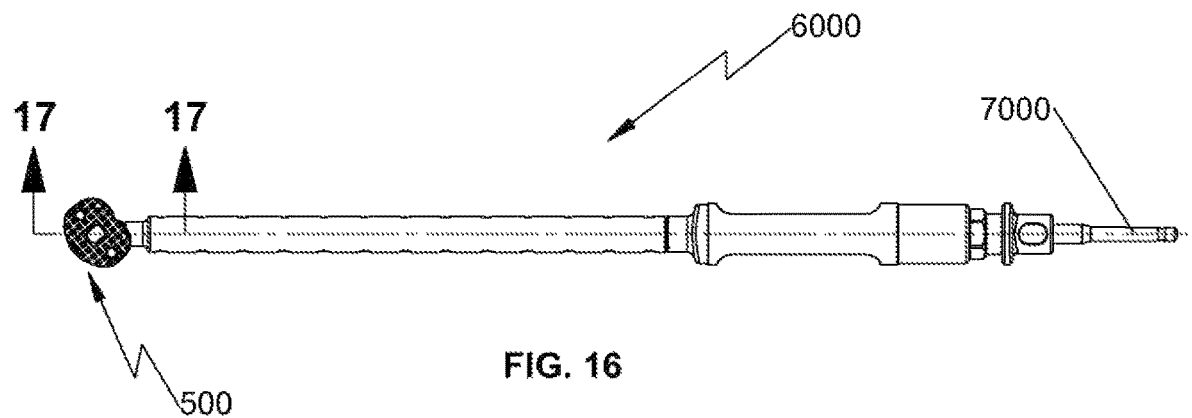
FIG. 16 is a top view of the insertion instrument of FIG. 10 illustrating use with the height adjusting driver of FIG. 13A with the spinal fixation device of FIG. 1.

In use, the clinician first distracts vertebral bodies of interest to establish the intervertebral space. The clinician may then remove vertebral tissue, if necessary or desired. First and second elongate members 666, 668 of end plate assembly 560 are selectively positioned to achieve a desired orientation of first end plate 540. Insertion instrument 6000 is coupled with spinal fixation device 500 by, e.g., threadably, coupling engaging portion 6032 (FIG. 17) with bore 521. Spinal fixation device 500 is then positioned adjacent a desired intervertebral space between vertebral bodies. Upon inserting spinal fixation device 500 in the intervertebral space, height adjusting driver 7000 can be inserted through channel 6035 (FIGS. 16 and 17) of insertion instrument 6000 to further adjust the axial distance between first end plate 560 and outer housing 510 by placing engaging portion 7030 through one of the plurality of bores 521 defined in outer housing 510 such that teeth 7032 of engaging portion 7030 of height adjusting driver 7000 engages teeth 684, 682 of first and second rotatable members 610, 612 of mounting assembly 600, respectively. In this manner, rotation of handle 7010 causes rotation of first and second rotatable members 610, 612 in opposite directions, which, in turn, imparts axial translation of first and second elongate members 666, 668. In this manner, the clinician may adjust the axial distance between first end plate 540 and outer housing 510, i.e., height of spinal fixation device 500. Handle 7010 is rotated until a desired height of spinal fixation device 500 is effected through axial movement of end plate assembly 560.

In addition, after removing height adjusting driver 7000 from insertion instrument 6000, angle adjusting driver 8000 can be inserted through channel 6035 (FIG. 19) of insertion instrument 6000 to further adjust the angular orientation of first end plate 540 with respect to outer housing 510. Engaging portion 8030 is inserted through one of the plurality of bores 521 defined in outer housing 510 such that teeth 8034 of engaging portion 8030 of angle adjusting driver 8000 engages teeth 682 of first rotatable member 610 or teeth 684 of second rotatable member 612 of mounting assembly 600. Rotation of handle 8010 causes rotation of one of the first or second rotatable members 610, 612 of mounting assembly 600, which, in turn, causes translation of one of first or second elongate members 666, 668. Relative movement between first and second elongate members 666, 668 enables the clinician to adjust the angular orientation of first end plate 540 with respect to outer housing 510 to achieve the desired lordosis or kyphosis. It is contemplated that the clinician may make further adjustments by alternating height adjusting driver 7000 and angle adjusting driver 8000 to achieve the desired length of spinal fixation device 500 and angular orientation of first end plate 540. Upon achieving the desired length of spinal fixation device 500 and angular orientation of first end plate 540, screw 190 may be placed in bore 521 defined in outer housing 510 through channel 6035 of insertion instrument 6000. Screw 190 may be threadably secured in bore 521 by using tapered driver 9000.

At this time, rod connector 1000, pedicle screws 1600, and spinal rod 1500 may be utilized to further secure spinal fixation device 500 between vertebral bodies and to further promote spinal fusion. Anchoring portion 1010 of rod connector 1000 is threadably coupled with bore 527 of spinal fixation device 500, and pedicle screws 1600 are secured with respective vertebral bodies. Thereafter, spinal rod 1500 is inserted through recessed portion 1032 of rod connector 1000 and respective pedicle screws 1600. At this time, rod connector 1000 may be adjusted for proper angular orientation. Screw 1040 may be used to secure spinal rod 1500 in recessed portion 1032 of rod connector 1000 and the set screws (not shown) may be used to secure spinal rod 1500 with pedicle screws 1600. At this time, additional rod connector 1000 may be used to further secure spinal fixation device 500 between vertebral bodies. At this time, additional spinal rod 1500 may be utilized to further secure spinal fixation device 500 (FIG. 24).

Based on the needs of the patient, drug delivery assemblies 1700, 1800, 1900, 3000 may be utilized to deliver the necessary drugs to the patient. To this end, drug reservoir 1720 of drug delivery assembly 1700 is secured with bore 527 of spinal fixation device 500. Supply port 1740 may be affixed to a location most convenient for the patient or the clinician to supply the drugs using, e.g., syringe 1750. Alternatively, cannula 1810 of drug delivery assembly 1800 is secured with bore 527 of spinal fixation device 500. The patient or the clinician may administer the drugs using syringe 1750. The use of drug delivery assemblies 1900, 2000 is substantially identical to the use of drug delivery assemblies 1700, 1800, and thus, will not be described herein. It is also contemplated that a drug pump such as, e.g., an insulin pump, may be connected to catheter 1730 to supply the drugs.

Although the illustrative embodiments of the present disclosure have been described herein with reference to the accompanying drawings, the above description, disclosure, and figures should not be construed as limiting, but merely as exemplifications of particular embodiments. For example, while the angular orientation of first end plate 560 is shown to be adjustable in cephalad and caudad directions, it is also contemplated that first end plate 560 may be adjustable in the medial and lateral directions. It is to be understood, therefore, that the disclosure is not limited to those precise embodiments, and that various other changes and modifications may be effected therein by one skilled in the art without departing from the scope or spirit of the disclosure.

What is claimed is:

1. A spinal fusion method comprising:
    attaching an engagement portion of a surgical instrument to an aperture in an outer housing of a spinal fixation device, the surgical instrument having a channel extending therethrough and the housing coupled with an end plate assembly;
    manipulating the surgical instrument to place the spinal fixation device between vertebral bodies;
    moving at least one of a first and second elongate member each pivotably coupled to a first end plate of the end plate assembly such that the first end plate moves and engages one of the vertebral bodies, wherein the first elongate member receives a portion of the second elongate member;
    moving one or both of the first and second elongate members to transition the first end plate from a first angular orientation to a second angular orientation; and
    removing the surgical instrument from engagement with the spinal fixation device.

2. The method of claim 1, further comprising contacting the first end plate with one of the vertebral bodies.

3. The method of claim 2, further comprising engaging teeth on first and second rotatable members with a corresponding engaging portion of at least one height adjusting driver and angle adjusting driver.

4. The method of claim 2, further comprising axially moving the first and second elongate members to cause axial displacement of the first end plate with respect to the second end plate.

5. The method of claim 1, further comprising inserting at least one of a height adjusting driver and angle adjusting driver into the channel of the spinal fixation device to mate with an engagement portion.

6. The method of claim 5, further comprising rotating the at least one height adjusting driver and angle adjusting driver to mate the engaging portion with the teeth of the first and second rotatable members.

7. The method of claim 1, further comprising inserting an angle adjusting driver into a bore defined by an outer wall of the outer housing.

8. The method of claim 1, further comprising inserting a height adjusting driver into a bore defined by the outer wall of the outer housing.

9. A method for stabilizing a spine during surgery, the method comprising:
    attaching an engagement portion of a surgical instrument to an aperture in an outer housing of a spinal fixation device, the housing coupled with an end plate assembly;
    manipulating the surgical instrument to insert the spinal fixation device between vertebral bodies;
    moving at least one of a first and second elongate member each pivotably coupled to a first end plate of the end plate assembly such that the first endplate moves and engages one of the vertebral bodies, wherein the first elongate member receives a portion of the second elongate member;
    moving one or both of the first and second elongate members to transition the first end plate from a first angular orientation to a second angular orientation;
    coupling a rod connector having an anchoring portion and a head portion with the outer housing of the spinal fixation device; and
    inserting the spinal rod into the head portion of the rod connector.

10. The method of claim 9, further comprising coupling an anchoring portion of the rod connector with a bore defined by the spinal fixation device.

11. The method of claim 9, further comprising inserting a screw into a bore of the head portion of the rod connector to secure the spinal rod thereto.

12. The method of claim 9, further comprising coupling a second rod connector with a bore of the outer housing.

13. The method of claim 12, further comprising inserting a second spinal rod into a head portion of the second rod connector.

14. The method of claim 9, further comprising attaching the spinal rod to a pedicle screw.

15. A method for delivering drugs into a spinal cavity during surgery, the method comprising:
    attaching a spinal fixation device having an outer housing and adjustable end plate coupled with the outer housing to a surgical instrument;
    inserting the spinal fixation device into the spinal cavity using the surgical instrument;
    moving at least one a first and second elongate member each pivotably coupled to the end plate such that the end plate moves and engages the vertebral bodies, wherein the first elongate member receives a portion of the second elongate member;
    moving one or both of the first and second elongate members to transition the first end plate from a first angular orientation to a second angular orientation; and
    attaching a drug delivery assembly having a drug reservoir and a catheter to at least one of the spinal fixation device and rod connector.

16. The method of claim 15, further comprising attaching a supply port to at least one of the catheter and a syringe.

17. The method of claim 15, further comprising injecting drugs from a syringe into a supply port and the catheter.

18. The method of claim 15, further comprising coupling a second catheter to a supply port.

19. The method of claim 15, further comprising attaching a shield to the spinal fixation device to reduce radiation to the spinal cord.

* * * * *